(12) United States Patent
Francis et al.

(10) Patent No.: US 10,137,223 B2
(45) Date of Patent: Nov. 27, 2018

(54) ALIGNED FIBER AND METHOD OF USE THEREOF

(71) Applicant: LifeNet Health, Virginia Beach, VA (US)

(72) Inventors: Michael Francis, Virginia Beach, VA (US); Roy Ogle, Virginia Beach, VA (US)

(73) Assignee: LifeNet Health, Virginia Beach, VA (US)

( * ) Notice: Subject to any disclaimer, the term of this patent is extended or adjusted under 35 U.S.C. 154(b) by 214 days.

(21) Appl. No.: 14/776,106

(22) PCT Filed: Mar. 13, 2014

(86) PCT No.: PCT/US2014/025636
§ 371 (c)(1),
(2) Date: Sep. 14, 2015

(87) PCT Pub. No.: WO2014/160019
PCT Pub. Date: Oct. 2, 2014

(65) Prior Publication Data
US 2016/0022865 A1   Jan. 28, 2016

Related U.S. Application Data

(60) Provisional application No. 61/785,031, filed on Mar. 14, 2013.

(51) Int. Cl.
*A61K 38/17*        (2006.01)
*C07K 1/00*         (2006.01)
(Continued)

(52) U.S. Cl.
CPC ............... *A61L 27/18* (2013.01); *A61L 27/24* (2013.01); *A61L 27/26* (2013.01);
(Continued)

(58) Field of Classification Search
None
See application file for complete search history.

(56) References Cited

U.S. PATENT DOCUMENTS

| | | | |
|---|---|---|---|
| 2002/0090725 A1* | 7/2002 | Simpson | A61L 15/32 435/402 |
| 2004/0037813 A1* | 2/2004 | Simpson | A61F 2/08 424/93.7 |

(Continued)

FOREIGN PATENT DOCUMENTS

| | | |
|---|---|---|
| WO | 2010016942 A1 | 2/2010 |
| WO | 2012027592 A2 | 3/2012 |

(Continued)

OTHER PUBLICATIONS

Zeugolis, D.I., et al., "Electro-spinning of pure collagen nano-fibres—Just an expensive way to make gelatin?", Mar. 3, 2008, pp. 2293-2305, vol. 29(15), Biomaterials, Elsevier Science Publishers.

(Continued)

*Primary Examiner* — Christopher R Tate
*Assistant Examiner* — Douglas F White
(74) *Attorney, Agent, or Firm* — RatnerPrestia

(57) ABSTRACT

A scaffold comprising an aligned fiber. The invention further relates to a scaffold comprising one or more electrospun fibers wherein a fast Fourier transform (FFT) analysis result of the fibers have adjacent major peaks with about 180? apart from each other. Methods for promoting differentiation of stem cells into osteoblasts, chondrocytes, ligament or tendon, the method comprising culturing the cells on the scaffold or aligned fiber in conditions suitable for the cell differentiation.

15 Claims, 10 Drawing Sheets

(51) Int. Cl.
| | |
|---|---|
| *C07K 14/00* | (2006.01) |
| *C07K 16/00* | (2006.01) |
| *C07K 17/00* | (2006.01) |
| *C09H 1/00* | (2006.01) |
| *A61L 27/18* | (2006.01) |
| *A61L 27/24* | (2006.01) |
| *A61L 27/26* | (2006.01) |
| *A61L 27/36* | (2006.01) |
| *A61L 27/38* | (2006.01) |
| *A61L 27/56* | (2006.01) |
| *D01D 5/00* | (2006.01) |
| *C12N 5/079* | (2010.01) |
| *A61F 2/08* | (2006.01) |

(52) U.S. Cl.
CPC ....... *A61L 27/3604* (2013.01); *A61L 27/3633* (2013.01); *A61L 27/38* (2013.01); *A61L 27/383* (2013.01); *A61L 27/56* (2013.01); *C12N 5/0618* (2013.01); *D01D 5/0076* (2013.01); *D01D 5/0092* (2013.01); *A61F 2/08* (2013.01); *A61F 2240/001* (2013.01); *A61L 2400/12* (2013.01); *C12N 2533/30* (2013.01); *C12N 2533/54* (2013.01); *C12N 2533/90* (2013.01)

(56) References Cited

U.S. PATENT DOCUMENTS

| | | | |
|---|---|---|---|
| 2007/0225631 A1* | 9/2007 | Bowlin | A61K 38/363 602/52 |
| 2008/0213389 A1 | 9/2008 | Lelkes | |
| 2009/0018643 A1* | 1/2009 | Hashi | A61F 2/82 623/1.15 |
| 2010/0233115 A1 | 9/2010 | Patel et al. | |
| 2011/0236974 A1 | 9/2011 | Ogle et al. | |
| 2012/0221025 A1 | 8/2012 | Simpson et al. | |
| 2012/0273993 A1* | 11/2012 | Shoseyov | A61L 27/24 264/202 |

FOREIGN PATENT DOCUMENTS

| | | |
|---|---|---|
| WO | 2013033680 A1 | 3/2013 |
| WO | 2013119873 A1 | 8/2013 |

OTHER PUBLICATIONS

European Communication for European Application No. 14 773 677.1, dated Nov. 6, 2017, 8 pages.

Huang et al. (2011) Electrospun Collagen-Chitosan-TPU Nanofibrous Scaffolds for Tissue Engineered Tubular Grafts, Colloids Surf. B. Biointerfaces, 82:307-315.

International Search Report and Written Opinion dated Jul. 10, 2014; International Application No. PCT/US2014/025636.

Supplementary European Seach Report for European Application No. 14773677.1, dated Oct. 25, 2016, 3 pages.

Extended Search Report for European Application No. 14773677.1, dated Oct. 7, 2016, 6 pages.

Anderson et al., "Biodegradation and Biocompatibility of PLA and PLGA Microspheres", Advanced Drug Delivery Reviews, 1997, vol. 28, pp. 5-24.

Ayres et al., "Measuring Fiber Alignment in Electrospun Scaffolds: A User's Guide to the 2D Fast Fourier Transform Approach," Journal of Biomaterials Science, Polymer Edition, (2008), vol. 19, No. 5, pp. 603-621.

Behravesh et al., "Synthetic Biodegradable Polymers for Orthopaedic Applications," Clinical Orthopaedics and Related Research, No. 367S, pp. S118-5125.

Cleek et al., "Microparticles of Poly(DL-lactic-co-glycolic acid)/poly(ethylene glycol) Blends for Controlled Drug Delivery," Journal of Controlled Release, vol. 48 1997 pp. 259-268.

Lu et al., "Polymeric Delivery Vehicles for Bone Growth Factors," 2000, Park & Mrsny; Controlled Drug Delivery, ACS Symposium Series; American Chemical Society, pp. 124-138.

Schnaper et al., "Regulation of Cell Function by Extracellular Matrix," Pediatr. Nephrol, 1993, vol. 7—pp. 96-104.

* cited by examiner

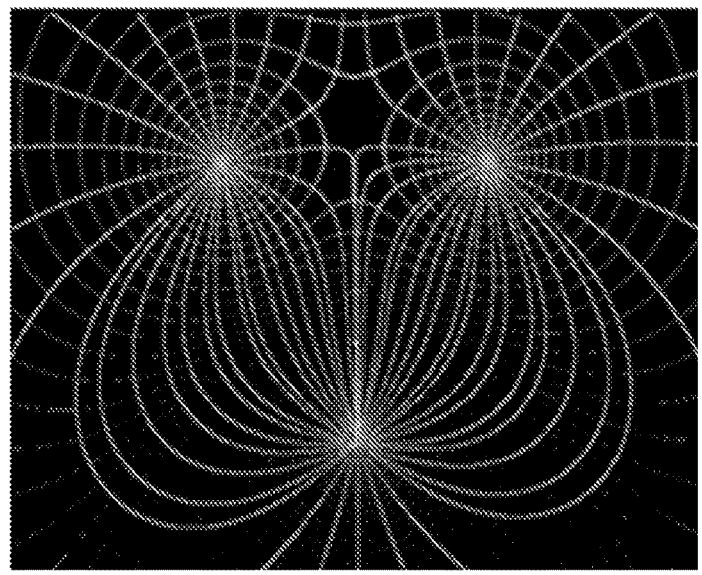
FIG. 1A
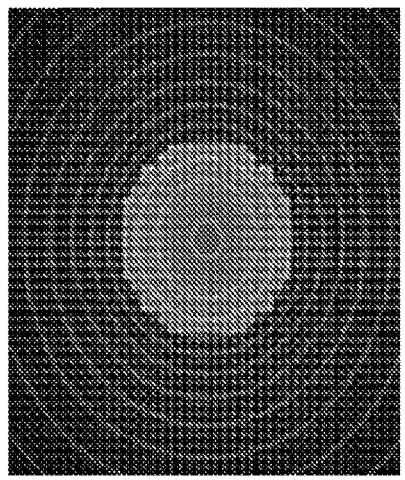 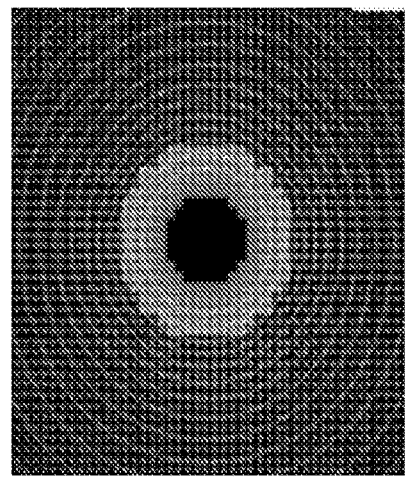
FIG. 1B          FIG. 1C

ALIGNED FIBER AND METHOD OF USE THEREOF

BACKGROUND OF THE INVENTION

The invention relates to an aligned fiber and method of use thereof.

SUMMARY OF THE INVENTION

The invention relates to a scaffold comprising an aligned fiber. The invention further relates to a scaffold comprising one or more electrospun fibers. In some embodiments, wherein a fast Fourier transform (FFT) analysis result of the fibers have adjacent major peaks with about 180° apart from each other.

The invention further relates to methods culturing cells on the scaffold or aligned fiber described herein.

The invention also relates to methods of promoting differentiation of stem cells into osteoblasts, chondrocytes, ligament or tendon, the method comprising culturing the cells on the scaffold or aligned fiber described herein in conditions suitable for the cell differentiation

DETAILED DESCRIPTION OF THE INVENTION

Figure 1D:
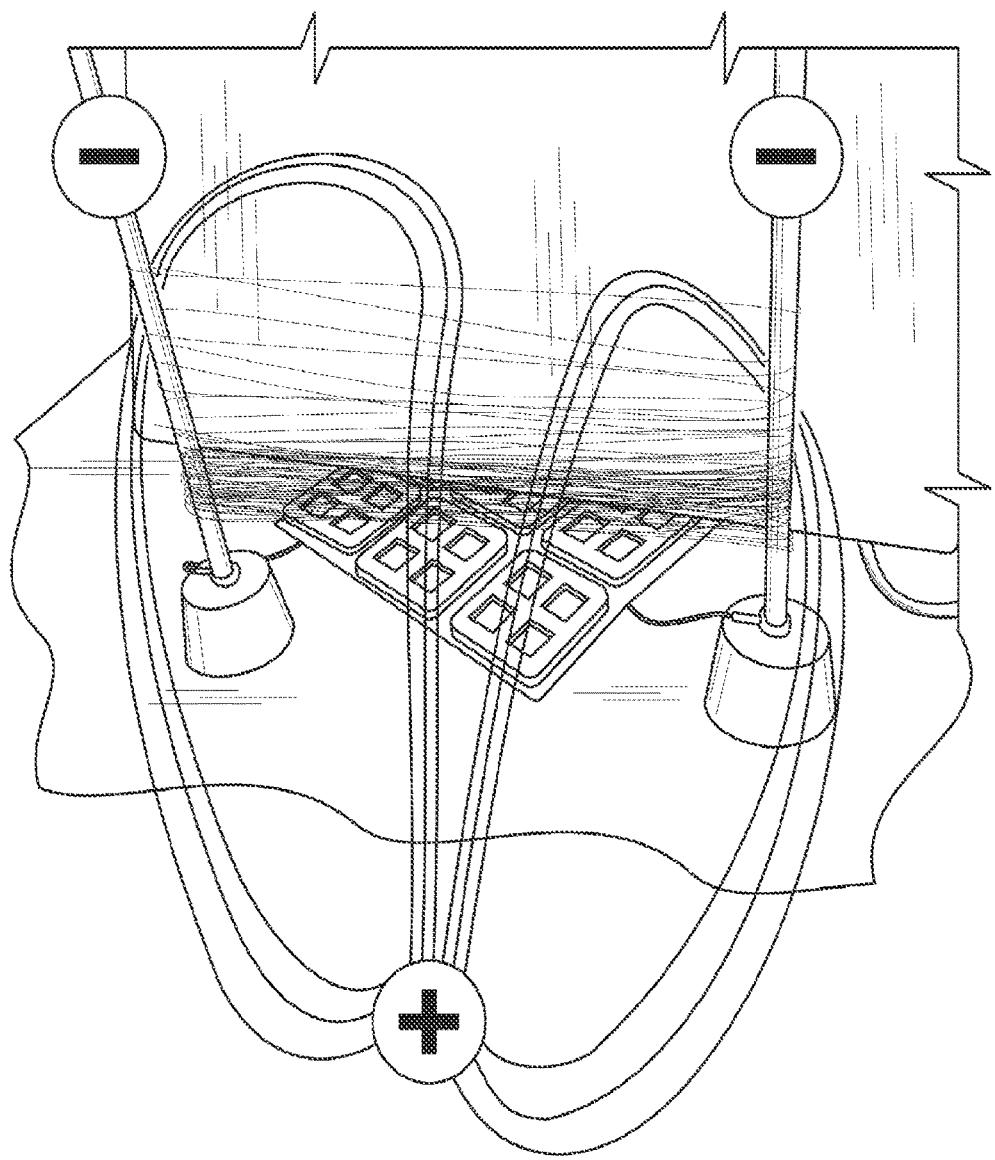
FIG. 1 depicts representative field lines that are modulated between a split point negative voltage sources and a single positive voltage source (A, D), aiding in imparting alignment in the electrospinning scheme. The change in field lines between a solid (B) and hollow (C) rod is also modeled.

The invention relates to an electrospinning apparatus comprising (i) at least one spinneret comprising an electrified tip; and (ii) a collector comprising two rods and a platform connected to the two rods, wherein the two rods are configured split an electric field between them. In one aspect, the spinneret comprising an electrified tip may have two, three, four, five or more electrified tips. In another aspect, the collector comprising two rods may have three, four, five or more rods. In additional aspect, the platform connected to the two rods may have three, four, give or more rods connected to the platform. As defined herein, "comprising two rods" refers to comprising at least two rods, including, for example, two, three, four, and five rods.

The invention also relates to an electrospinning apparatus comprising (i) two spinnerets, each of which comprises a tip electrified with an opposite charge to one another; and (ii) a collector comprising two rods and a platform connecting the two rods, wherein the two rods are grounded.

Electrospray/electrospinning techniques can be used to form particles and fibers as small as one nanometer in a principal direction. The phenomenon of electrospray involves the formation of a droplet of polymer melt at an end of a needle, the electric charging of that droplet, and an expulsion of parts of the droplet because of the repulsive electric force due to the electric charges. In electrospraying, a solvent present in the parts of the droplet evaporates and small particles are formed but not fibers. The electrospinning technique is similar to the electrospray technique. In electrospinning and during the expulsion, however, fibers are formed from the liquid as the parts are expelled.

In particular, for example, the electrospinning typically involves a polymer solution (or melt) maintained at its surface tension on the tip of a nozzle via a syringe in a pump. When sufficiently high voltage is introduced (e.g. 15-40 kV) to the polymer or oligomer in solution to create a charge imbalance, the solution may be drawn towards a grounded collector through the static electric field. As the polymer erupts from the needle and the assembling polymer whip through space, the fiber may be subjected to a series of stretching and bending instabilities, resulting in plastic stretching and elongation to minimize these instabilities generated by repulsive electrostatic forces. As the polymer or oligomer travels through space and rapidly thins into a fine stream, the solvent may evaporate and the polymer or oligomer assembles into fibers, leaving dry nano- to micro-scale fibers of tailorable physical attributes on the collector in the typical electrospinning scheme. Additionally, when high electrical potential is applied to a low viscosity polymer or oligomer melt or solution, or when improperly high or low voltage is applied, electrospraying may occur, which is typified by the polymer jet breaking down into fine droplets. It is therefore possible to produce particles or nano- to micro-sphere particles, fibers and bead-and-string type structures via this process from simply altering the solution or electrospinning parameters. Polymer solution properties, applied electrical potential, polymer molecular weight, polymer solution flow rate, distance between spinner and collector, ambient parameters (e.g. humidity, air velocity, temperature) and motion of the collecting target can be altered to form fibers of controlled fiber distribution, diameter and alignment via electrospinning.

The electrospinning apparatus as described herein in one aspect may include one or more spinneret. The term "spinneret" used herein refers to a single- or multi-pored device through which a polymer or oligomer solution is extruded to form fibers. In one aspect, the spinneret is selected from the group consisting of a multiple nozzle spinneret, a single syringe or capillary spinneret, and a compound spinneret. In another aspect, the spinnerets of the electrospinning apparatus may be differently charged, resulting in differently charged polymer or oligomer solutions extruded from them. For example, different voltages may be applied to two or more polymer or oligomer sources whereby a positively charged solution is combined in space with a negatively charged solution, which is sent to the grounded rotating rods of the mandrel.

The electrospinning apparatus according to some embodiments of the present invention includes at least one spinneret comprising an electrified tip. The spinneret may have an electrified tip having a charge, and the tip may have one or more pores. In some embodiments, the electrospinning apparatus may include two or more tips having different charges. In particular, for example, the electrospinning apparatus may include two tips having opposite charges to each other.

In some embodiments, the spinneret described herein may be replaced with a different ejecting device comprising a drum configured to rotate in contact with a reservoir of a polymer or oligomer solution herein. In one aspect, this drum may pull the polymer or oligomer solution as a thin film on the surface of the drum. In another aspect, the drum may be charged, resulting in charging of the solution. In additional embodiments, the spinneret described herein may be replaced with a different ejecting device comprising a flat surface in contact with a polymer or oligomer solution, and the polymer or oligomer solution may form a polymer bubble(s) by applying air.

The electrospinning apparatus in one aspect may include a collector having at least two rods and a platform. In some embodiments, the collector may have, for example, three, four, five, six, seven, eight, nine, ten, twenty, thirty, or forty rods. Herein, the term "rod" used herein refers to a bar of material having a shape including, but not limited to prism, cylinder, pentagonal rod, hexagonal rod, square rod, and triangular rod. The rod may comprise an electrical conducting material (e.g. a metal). In some embodiments, the rod may be electrified with a charge opposite to a charge of the electrified tip extruding a solution to the rod. In another aspect, the rod may be made of a non-electrical conducting material (e.g. insulating plastic). In further aspect, the rod may be made of both electrical and non-electrical conducting materials. For example, the electrical conducting material may be coated on the non-electrical conducting material.

The rod described herein may be directly or indirectly connected and/or fixed to a platform. The platform refers to any support for the rod. In one aspect, the rod comprises a proximal part and distal end, and the proximal part and/or distal end may be connected and/or fixed to the platform. In another aspect, the rod may go through the platform to which the proximal part of the rod is connected and/or fixed.

In one aspect, the platform may be a part of a machine frame. In another aspect, the electrospinning apparatus described herein may further include a chamber enclosing the spinneret and the collector. The chamber may comprise the platform described herein. In another aspect, the platform may consist of or comprise a rotating shaft or a bearing that is directly or indirectly connected and/or fixed to the rod.

The platform according to some embodiments includes a bearing connected to the rod described herein. The bearing used herein refers to a guide for rotating the rod. In one aspect, the bearing may be a rotating shaft. In another aspect, the platform or the bearing used herein may use plain bearing, rolling-element bearings, jewel bearings, fluid bearings, magnetic bearings, and/or flexure bearings. The bearing may include an electrical conductor configured to allow electrical conductance to the rods. For example, the bearing may have mercury.

In another aspect, the platform connected to the rod(s) may be configured to spin resulting in rotation of the rod(s) about the spinning axis of the platform. In some embodiments, the rods are configured to rotate at between about 0 and about 8000 RPM, between about 0 and about 7000 RPM, between about 0 and about 6000 RPM, between about 0 and about 5000 RPM, between about 0 and about 4000 RPM, between about 0 and about 3000 RPM, between about 0 and about 2000 RPM, between about 0 and about 1000 RPM, between about 0 and about 500, between about 0 and about 300 RPM, between about 0 and about 100 RPM, between about 0 and about 50, between about 1 and about 2000 RPM, between about 1 and about 1000 RPM, between about 1 and about 500, between about 1 and about 300 RPM, between about 1 and about 100 RPM, between about 1 and about 50, between about 1000 and about 8000 RPM, between about 2000 and about 8000 RPM, between about 3000 and about 8000 RPM, between about 4000 and about 8000 RPM, between about 5000 and about 8000 RPM, between about 1000 and about 6000 RPM, between about 2000 and about 6000 RPM, or between about 3000 and about 6000 RPM. In additional embodiments, the rods are configured to rotate at about 50 RPM, about 500 RPM, about 1500 RPM, about 2500 RPM, about 3500 RPM, about 4500 RPM, about 5500 RPM, about 6500 RPM, about 7500 RPM or lower. In additional embodiments, the rods are configured to rotate at about 500 RPM, about 1500 RPM, about 2500 RPM, about 3500 RPM, about 4500 RPM, about 5500 RPM, about 6500 RPM, about 7500 RPM or higher. In some embodiments, when the rods are rotating, the fibers may spin around the rods. In other embodiments, when the rods are rotating, the fibers may also move or jump from one rod to another rod. In yet additional embodiments, the rods are stationary. In yet further embodiments, when the rods are stationary, the fibers may move or jump from one rod to another through an electric field.

In some embodiments, an air driven (pneumatic) motor and an electric (DC) motor may be employed in the electrospinning. In further embodiments, the pneumatic motor may generate less stray field anomalies and allow capturing of more nanofiber product on the rod(s) compared to the DC motor.

In one aspect, the fibers align on the rod (e.g. by spinning around the rods or jumping to one rod to another) in a perpendicular angle to the rods. In another aspect, the fibers align in an angle about 91, 92, 93, 94, 95, 100, 105, 110, 115, 120, 125, 130, 135, 140, 145, 150, 155° or less. In another aspect, the fibers align in an angle about 90, 91, 92, 93, 94, 95, 98, 103, 108, 113, 118, 123, 128, 133, 138, 143, 148, 153° or more. In another aspect, the fibers align in an angle between about 90 and about 93°, between about 90 and about 95°, between about 90 and about 100°, between about 90 and about 105°, between about 90 and about 110°, between about 90 and about 115°, between about 93 and about 95°, between about 93 and about 100°, between about 93 and about 105°, between about 93 and about 110°, or between about 93 and about 115°.

As used herein, the term "about" modifying, for example, the quantity of an ingredient in a composition, concentrations, volumes, process temperature, process time, yields, flow rates, pressures, and like values, and ranges thereof, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of, for example, a composition, formulation, or cell culture with a particular initial concentration or mixture, and amounts that differ due to mixing or processing a composition or formulation with a particular initial concentration or mixture. Whether modified by the term "about" the claims appended hereto include equivalents to these quantities. The term "about" further may refer to a range of values that are similar to the stated reference value. In certain embodiments, the term "about" refers to a range of values that fall within 10, 9, 8, 7, 6, 5, 4, 3, 2, 1 percent or less of the stated reference value.

The electrospinning apparatus according to some embodiments of the present invention includes a collector comprising two or more rods and a platform connected to the rods, wherein the rods are configured split an electric field between them. In one aspect, operating the electrospinning apparatus described herein may result in forming a point charge splitting of an electric field, through which traveling polymer or oligomer solutions align. In another aspect, the rods may be grounded.

The split electric field in some embodiments is separated by an air insulator. In one aspect, with air as an insulator between electrically charged metal rods, electrospun fibers are collect between opposed metal rods in an aligned fashion. The electrospun fiber described herein may be a microfiber or a nanofiber.

The split electric field in some embodiments is insulated by non-conductive materials or environments placed between the rods (e.g. carbon fiber, PTFE [Teflon], mica, diamond, ceramic, rubbers, glass, vacuum, materials on the low ends of the triboelectric series in the high resistivity range, also including paper, cotton, wood, epoxy, plastics such as: ABS [acrylonitrile, butadiene, and styrene], polycarbonate, acetate, acrylic, delrin, fiberglass, FEP, high impact polystyrene [HIPS], kapton, kaptrex, kynan, macor, melamine, meldin 7001 unfilled polyimide, MICA, neoprene, nomex, noryl PPO, PolyEtherEther-Ketone [PEEK], polyethylene terephthalate [P.E.T], P.E.T.G, phenolics such as micarta phenolics, perfluoroalkoxy [PFA], Polycarbonate, polyester [mylar], polyolefins, polystyrene, polysufone, polyurethane,), Rexolite® 1422 &220, polyphenylene sulfide [Ryton], silicone/fiberglass, silicone rubber, techtron, Ultem® 1000, Vespel® SP-1 [polyimide], electrically insulating papers such as vulcanized fibre, tapes from the above materials, and foams of these materials, including neoprene foam, polystyrene foam, polyurethane foam, silicone foam, vinyl foam.

The term microfiber as used herein means a fiber comprising a diameter of about 1000 µm or less. The term nanofiber as used herein means a fiber comprising a diameter of about 1000 nm or less. Relative to the parent bulk material, nano-features can impart many extraordinary properties to macrostructures, including superior mechanical, electrical, optical and magnetic properties, adding surface functionality and yielding high surface area. Matrices of nanofibers of varying diameters may show a range of variable surface properties (e.g. hydrophobicity and hydrophilicity), porosities, and usually superior mechanical properties (e.g. tensile strength, stiffness) relative to the material in other forms.

In some embodiments, the nanofiber described herein may have an average diameter of about 1000 nm or less, 900 nm or less, 800 nm or less, 700 nm or less, 600 nm or less, 500 nm or less, 400 nm or less, 300 nm or less, 200 nm or less, 100 nm or less, 50 nm or less, 20 nm or less, or 10 nm or less. In some embodiments, the nanofiber described herein may have an average diameter of about 1000 nm or more, 900 nm or more, 800 nm or more, 700 nm or more, 600 nm or more, 500 nm or more, 400 nm or more, 300 nm or more, 200 nm or more, 100 nm or more, 50 nm or more, 20 nm or more, 10 nm or more, or 1 nm or more.

In some embodiments, the microfiber described herein may have an average diameter of about 1000 µm or less, 900 µm or less, 800 µm or less, 700 µm or less, 600 µm or less, 500 µm or less, 400 µm or less, 300 µm or less, 200 µm or less, 100 µm or less, 50 µm or less, 20 µm or less, or 10 µm or less. In some embodiments, the microfiber described herein may have an average diameter of about 1000 µm or more, 900 µm or more, 800 µm or more, 700 µm or more, 600 µm or more, 500 µm or more, 400 µm or more, 300 µm or more, 200 µm or more, 100 µm or more, 50 µm or more, 20 µm or more, 10 µm or more, or 1 µm or more.

In some embodiments, the rods described herein may be set parallel to each other in the electrospinning apparatus. In other embodiments, the rods may not be set parallel to each other but at an angle, for example, at an angle smaller than 5°, 10°, 30°, 50°, 70°, or 90°. In other embodiments, the rods may not be set parallel to each other but at an angle, for example, at an angle bigger than 1°, 8°, 25°, 40°, 60°, or 75°. In additional embodiments, the rod described herein may be straight, curved or angled.

The rods described herein in some embodiments are separated from one another by an average distance of about 1 cm, about 2 cm, about 3 cm, about 5 cm, about 8 cm, about 10 cm, about 13 cm, about 15 cm, about 18 cm, about 20 cm, about 23 cm, about 25 cm, about 27 cm, about 30 cm or more. In one aspect, the rods are separated from one another by an average distance of about 1 cm, about 2 cm, about 3 cm, about 5 cm, about 8 cm, about 10 cm, about 13 cm, about 15 cm, about 18 cm, about 20 cm, about 23 cm, about 25 cm, about 27 cm, about 30 cm, about 40 cm, about 50 cm, about 60 cm or less. In another aspect, the rods are separated from one another by a distance from about 1 cm to about 25 cm, from about 6 cm to about 25 cm, from about 12 cm to about 25 cm, from about 18 cm to about 25 cm, from about 23 cm to about 25 cm, from about 1 cm to about 35 cm, from about 6 cm to about 35 cm, from about 12 cm to about 35 cm, from about 18 cm to about 35 cm, from about 24 cm to about 35 cm, or from about 10 cm to about 20 cm.

The collector may be biocompatible. In fact, any of the other elements of the electrospinning apparatus described herein may be biocompatible.

The electrospinning apparatus described herein may also include a control mechanism configured to control the electric potential of the electrified tip. The electrospinning apparatus described herein may also include a reservoir for a solution. The electrospinning apparatus described herein may also include an electric source connected to the electrified tip.

The invention further relates to methods of electrospinning using the electrospinning apparatus described herein and methods of preparing an electrospun fiber by the electrospinning. The methods of electrospinning and methods of preparing an electrospun fiber by the electrospinning may comprise (i) extruding a solution from an electrified tip of a spinneret, and (ii) collecting the extruded solution on at least a part of a collector. The methods of electrospinning or preparing an electrospun fiber by the electrospinning may further comprise extruding two, three or more solutions from one, two, three or more electrified tips of a spinneret. The methods of electrospinning or preparing an electrospun fiber by the electrospinning may further comprise extruding two, three or more solutions from one, two, three or more electrified tips of one, two, three or more spinnerets. The methods of preparing an electrospun fiber by the electrospinning may further comprise coating the extruded solution with another electrospun fiber prepared by the methods described herein.

The solution that may be extruded using the electrospinning apparatus described herein may include, but is not limited to, solutions comprising collagen type I, adipose extracellular matrix, heart basement membrane extract or extracellular matrix, placenta basement membrane extract or extracellular matrix, and polycaprolactone. Additional materials that may be electrospun by the method described herein include, but are not limited to, poly(glycolic acid), poly (lactic acid), polydioxanone, poly(lactide-co-glycolide) copolymers, polyesters polysaccharides, polyhydroxyalkanoates, starch, polylactic acid, cellulose, proteins, agar, silks, alginate, collagen/gelatin, carrageenan, elastin, pectin, resilin, konjac, adhesives, gums, polyamino acids, polysaccharides, soy, zein, wheat gluten, casein, chitin/chitosan, serum albumin, hyaluronic acid, lipids/s urfactants, xanthan, acetoglycerides, waxes, surfactants, dextran, emulsan, gelian, polyphenols, levan, lignin, curd, ian, tannin, polygalactosamine, humic acid, shellac, pullulan, poly-gamma-glutamic acid, elsinan, natural rubber, yeast glucans, and synthetic polymers from natural fats and oils, and the mixture thereof.

In one aspect, the collector of the electrospinning apparatus is a biocompatible support to be coated by the electrospun fiber on its surface and may be used as a part of the implant described herein. For example, the collector may comprise a bone matrix, and the electrospun fiber is collected on the surface of the bone matrix, resulting in coating of the bone matrix. The bone matrix may have two or more different electrospun fiber coatings on its surface.

The invention further relates to a method of coating a matrix on a surface comprising (i) extruding a solution from an electrified tip of a spinneret, and (ii) collecting the extruded solution on a portion of a collector, wherein the collector further comprises two rods and a platform connected to the two rods, the two rods are configured to split an electric field between them, and the portion of the collector comprises the matrix. The invention further relates to a method of coating a matrix on a surface comprising (i) extruding one or more solutions from electrified trips of two spinnerets, each of which comprises at least one tip electrified with an opposite charge to a tip of the other spinnerets, and (ii) collecting the extruded solution on a portion of a collector, wherein the collector further comprises two rods and a platform connected to the two rods, the two rods are grounded, and the portion of the collector comprises the matrix. In some embodiments, the matrix is a bone matrix, and the solution comprises a bone matrix solution. In additional embodiments, the matrix may comprise a synthetic surface.

In some embodiments, the matrix is biocompatible. In further embodiments, the biocompatible matrix is an implantable biocompatible matrix that can function as a support system for the bone matrix described herein. A biocompatible matrix should be non-toxic, non-eliciting or stimulating severe inflammatory response or immunological rejections, and devoid of other undesired reactions at the implantation site. In one embodiment, the biocompatible matrix is bone matrix or cartilage or connective tissue.

Figure 9A:
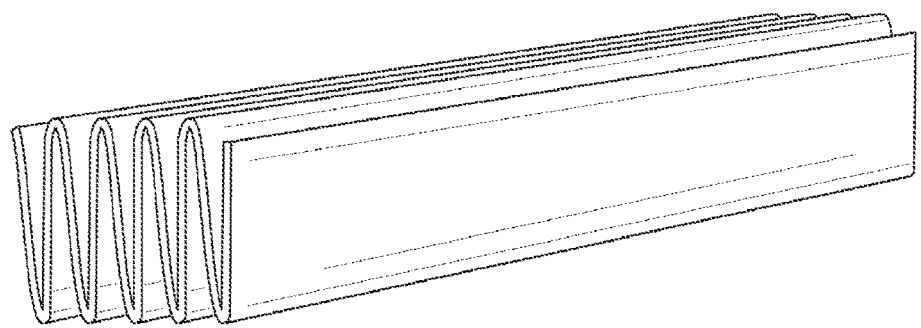
FIGS. 9A, 9B and 9C depict exemplary scaffolds prepared into an elongated roll by folding an elongated sheet (9A), an elongated roll by rolling an elongated sheet (9B), and a composite of multiple layers of elongated sheets (9C).
Figure 9B:
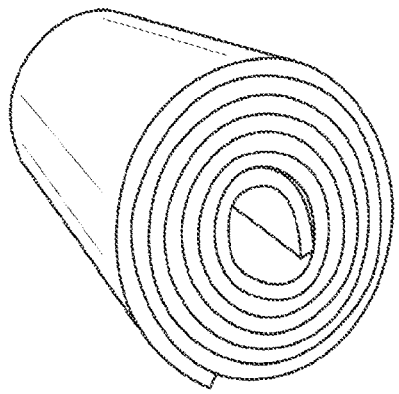
Figure 9C:
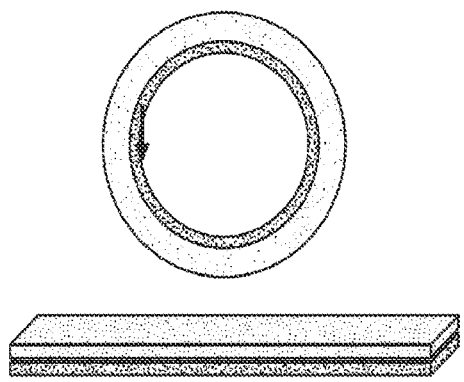

In some embodiments, the biocompatible matrix is prepared into a form of an elongated roll, an elongated sheet, a composite of multiple layers of sheets, or a combination thereof before or after being coated with the electrospun fibers. For example, the biocompatible matrix may be prepared as shown in FIGS. 9A, 9B, and 9C. In one aspect, the materials for the elongated roll and the elongated sheet may be different. In another aspect, the materials for each elongated sheet in the multiple layers of sheets may be different from each other. In another aspect, the electrospun fibers coated on the biocompatible matrix are aligned in one direction. For example, the electrospun fibers coated on the biocompatible matrix are aligned in the direction parallel or perpendicular to the length of the elongated sheet or the multiple layers. In another aspect, the biocompatible matrix is prepared by folding or rolling the sheet or sheets, along with the direction of nano fiber alignment to form an elongated roll implant. In one aspect, this biocompatible matrix in the form of an elongated sheet or a composite of multiple layers of sheets may be used to facilitate neuronal cell growth.

In some embodiments, the elongated roll implant may be prepared by combining a sheet or sheets to facilitate surgical implantation. The biomaterials to prepare the sheet and elongated roll may be the same, or different, as described previously.

In some embodiments, the elongated sheet described herein may have an average thickness of about 1000 μm or less, 900 μm or less, 800 μm or less, 700 μm or less, 600 μm or less, 500 μm or less, 400 μm or less, 300 μm or less, 200 μm or less, 100 μm or less, 50 μm or less, 20 μm or less, or 10 μm or less. In one aspect, the elongated sheet described herein may have an average thickness of about 1000 μm or more, 900 μm or more, 800 μm or more, 700 μm or more, 600 μm or more, 500 μm or more, 400 μm or more, 300 μm or more, 200 μm or more, 100 μm or more, 50 μm or more, 20 μm or more, 10 μm or more, or 1 μm or more.

In some embodiments, the length of the elongated sheet or roll implant is about 0.1 cm or more, about 0.3 cm or more, about 0.5 cm or more, about 0.7 cm or more, about 1 cm or more, about 2 cm or more, about 3 cm or more, about 5 cm or more, about 8 cm or more, about 10 cm or more, about 13 cm or more, about 15 cm or more, about 18 cm or more, about 20 cm or more, about 23 cm or more, about 25 cm or more, about 27 cm or more, or about 30 cm or more. In one aspect, the length of the elongated sheet or roll implant is about 1 cm or less, about 2 cm or less, about 3 cm or less, about 5 cm or less, about 8 cm or less, about 10 cm or less, about 13 cm or less, about 15 cm or less, about 18 cm or less, about 20 cm or less, about 23 cm or less, about 25 cm or less, about 27 cm or less, about 30 cm or less, about 40 cm or less, about 50 cm or less, or about 60 cm or less.

In some embodiments, the biocompatible matrix includes but is not limited to, bone graft implants, synthetic bone graft materials in forms of particulates, sheet, or blocks, tendon and/or ligament in bone tunnels, prosthetic implant, for example, for hip, shoulder, knee, or ankle, and trabecular metal. In further embodiments, the bone graft implants may include allograft or xeno-graft. In yet further embodiments, the bone graft implants may include structural bone implants including, but not limited to, monolithic or composite spinal implants (e.g., VERTIGRATs from LifeNet Health) and bone struts or blocks. In yet further embodiments, the bone graft implants may include demineralized, or non-demineralized bone particulates, including, but not limited to, cortical, cancellous, or cortical cancellous bone. In other embodiments, the electrospun fibers may be formed on cell or tissue culture surface.

Suitable biocompatible matrices include, but are not limited to, porous biocompatible scaffolds into which bone cells or progenitor cells may migrate. Osteogenic or chondrogenic cells, i.e., cells involved in the process of deposition of new bone material or cartilagenous material, respectively, can often attach to such porous biocompatible matrices, which can then serve as scaffolding for bone and cartilage tissue growth. Cells involved in the process of deposition of new ligament or tendon material can also attach to such porous biocompatible matrices. For certain applications, the biocompatible matrix should have sufficient mechanical strength to maintain its three dimensional structure and help support the immobilization of the bone segments being united or grafted together. Porous biocompatible matrices which provide scaffolding for tissue growth can accelerate the deposition of new bone or the rate of bone growth and are said to be "osteoconductive." Osteoconductive biocompatible matrices are especially useful in the matrices described herein. Porous biocompatible matrices which provide scaffolding for tissue growth can accelerate the deposition of new cartilage or the rate of cartilage growth and are said to be "chondroconductive." Osteoconductive biocompatible matrices are especially useful in the matrices described herein. Chondroconductive biocompatible matrices are especially useful in the matrices described herein. Angiogenic (or vasculogenic) biocompatible matrices are especially useful in the pharmaceutical compositions described herein. The osteoinductive, angiogenic or chondroinductive activity of the surface coated with the electrospun fibers or may not be altered, including but not limited to, enhanced activity, relative to a surface without the electrospun fiber coating or a natural surface without any coating. Thus, the osteoconductive, angiogenic or chondroconductive activity of the biocompatible matrices treated with the electrospun fibers of the present invention may be enhanced compared to matrices not treated with the bone matrix described herein. Of course, the biocompatible matrices are considered to be osteoconductive, angiogenic or chondroconductive if cells within the biocompatible matrix begin to differentiate into more osteoblast-like or chondrocyte-like appearing or functional cells, respectively.

The biocompatible matrices according to some embodiments of the present invention can be derived from natural sources or they can be synthetic or a mixture of both. Biocompatible matrices from natural sources may also comprise natural polymers, including, but not limited to, collagen, hyaluronic acid, alginate, albumin, fibrinogen-fibrin, chitosan, elasin, laminin, connective tissues, intervertebral disc, cortical or cancellous bone, demineralized or mineralized bone, fascia lata, dermis, muscle, ligament, tendon, cartilage including articular/hyaline cartilage, elastic cartilage, and fibrocartilage, a mixture thereof, and mixture of reconstituted tissue. Biocompatible matrices from synthetic sources refer to any material not produced by living organisms, which may include, not limited to, the synthetic material made up of organic components, inorganic components, or a mixture thereof. In some embodiments, a synthetic biocompatible matrix may comprise an organic synthetic polymer, such as poly(lactic-co-glycolic acid), polycaprolactone (PCL), polyglycolic acid (PGA), polylactic acid (PLA), polyhydroxybutyrate (PHB), Poly(ethylene glycol) (PEG), poly(ethylene oxide) (PEO)), and others. In some embodiments, a tissue, an organ, or biocompatible matrix comprising at least one of alginate, chitosan, collagen, gelatin, hyaluronic acid, a fibronectin, an elastin, a laminin, and a proteoglycan may be employed. In certain embodiments, a biocompatible matrix comprising inorganic components, such as hydroxyapatite, calcium sulfate, octacalcium phosphate, calcium phosphate, macroporous calcium metaphosphate ceramic, β-tricalcium phosphate, metal, metal alloy, and others, may be used. A biocompatible matrix used in certain embodiments of the present invention may be prepared by demineralizing, decellularizing or devitalizing a tissue or an organ and cells may be seeded onto the biocompatible matrix.

In some embodiments, the electrospun fibers described herein may be applied to a biocompatible matrix and may be incubated at conditions permitting the generation of a matrix that is partially or fully coated with the electrospun fibers. In some embodiments, incubation may be carried out at about 40° C. or lower, or between about 10° C. and about 37° C., or about 20° C. and about 37° C. Incubation may be carried out for between at least about 2 minutes and about 120 minutes, about 3 minutes and about 100 minutes, about 4 minutes and about 80 minutes, about 5 minutes and about 60 minutes, and about 5 minutes and about 30 minutes in certain embodiments. Incubation may be performed under static or dynamic conditions, such as with agitation, shaking, stirring, mixing, horizontal motion, rocking, and others.

In some embodiments of the present invention, a biocompatible matrix may be lyophilized before the electrospun fiber is applied to the biocompatible matrix. In certain embodiments, the electrospun fibers may be coated on the biocompatible matrix, and the coated matrix may be subsequently lyophilized. The lyophilized, coated matrix can then be rehydrated before it is used. Further, the cells can be seeded onto the matrix before implantation.

Examples of suitable osteoconductive or chondroconductive biocompatible matrices include but are not limited to, collagen (e.g., bovine dermal collagen), fibrin, calcium phosphate ceramics (e.g., hydroxyapatite and tricalcium phosphate), calcium sulfate, guanidine-extracted allogenic bone and combinations thereof. A number of suitable biocompatible matrices are commercially available, such as Collograft™ (Collagen Corporation), which is a mixture of hydroxyapatite, tricalcium phosphate and fibrillar collagen, and Interpore™ (Interpore International), which is a hydroxyapatite biomatrix formed by the conversion of marine coral calcium carbonate to crystalline hydroxyapatite.

A number of synthetic biodegradable polymers can serve as osteoconductive or chondroconductive biocompatible matrices with sustained release characteristics. Descriptions of these polymers can be found in Behravesh (1999) Clinical Orthopaedics 367, S118 and Lu (2000) Polymeric Delivery Vehicles for Bone Growth Factors in Controlled Drug Delivery: Designing Technologies for the Future, Park and Mrsny eds., American Chemical Society, which is incorporated herein in its entirety herein. Examples of these polymers include poly α-hydroxy esters such as polylactic acid/polyglycolic acid homopolymers and copolymers, polyphosphazenes (PPHOS), polyanhydrides and poly(propylene fumarates).

Polylactic acid/polyglycolic acid (PLGA) homo and copolymers are well known in the art as sustained release vehicles. The rate of release can be adjusted by the skilled artisan by variation of polylactic acid to polyglycolic acid ratio and the molecular weight of the polymer (see Anderson (1997) Adv. Drug Deliv. Rev. 28:5. The incorporation of PEG into the polymer as a blend to form microparticle matrices allows further alteration of the release profile of the active ingredient (see Cleek (1997) J. Control Release 48, 259). Ceramics such as calcium phosphate and hydroxyapatite can also be incorporated into the formulation to improve mechanical qualities.

In one embodiment, the biocompatible matrices used in the methods of the present invention are other types of bone matrices. For example, the electrospun fibers prepared by the methods described herein can be coated on a bone matrix. As used herein, the other types of the bone matrix may be a biocompatible matrix derived from or including elements of natural bone. In some embodiments, the natural bone is mineralized, partially demineralized, demineralized, cancellous, cortical, or cortical cancellous bone. The bone matrices used herein may or may not include additional synthetic components not typically found in bone tissue. Other embodiments include methods utilizing a biocompatible matrix derived from cartilage, other soft tissues such as the dermis, connective tissue, fascia, small intestine submucosa, serous membrane, pericardium, tendon, ligament, muscle, adipose tissue, myelin, blood vessels, base membrane, amniotic membrane and others. A biocompatible matrix prepared from hyaline cartilage, fibrocartilage or elastic cartilage, may be employed in some embodiments. A biocompatible matrix may be prepared from hyaline cartilage found in the condyle, tibial plateau, femoral head, humeral head, costal cartilage, or fibrocartilage found in intervertebral discs, or elastic cartilage found in the epiglottis or ear. In certain embodiments, a biocompatible matrix derived from natural sources that has been optionally cleaned, disinfected, chemically modified, decellularized, particulated, homogenized, lyophilized, gamma ray irradiated, and/or plasticized may be used. Any of the biocompatible matrices used herein may or may not include additional synthetic components not typically found in such tissue.

In one specific embodiment, the bone or cartilage biocompatible matrices may be demineralized or decellularized, respectively. Examples of demineralized matrices and methods of making are described in U.S. Pat. Nos. 6,189,537 and 6,305,379, which are incorporated herein in its entirety herein.

The biocompatible matrix, tissue, or organ used in certain embodiments of the present invention may be in the form of a powder, particulates, sheets, fibers, gels, putties, paste, blocks, cylinders, sponges, meshes, films, slices, curls, flakes, or wedges, among others. In certain embodiments of the present invention, the biocompatible matrix, tissue, or organ treated with the electrospun fibers by the methods described herein may be in the form of a powder, fibers, putty, or a sponge. In further embodiments, the sponge can include, for example, the implant having sponge-like structures disclosed in the co-pending, commonly-assigned patent application PCT/US09/04556 entitled "Composition for a Tissue Repair Implant and Methods of Making the Same" filed on Aug. 7, 2009, which is incorporated herein in its entirety herein. The treated matrices can be used in any of the methods of the present invention.

The invention also related to a method of preparing an electrospun fiber by electrospinning comprising (i) extruding a solution from an electrified tip of a spinneret, and (ii) collecting the extruded solution on a portion of a collector comprising two rods and a platform connected to the two rods, wherein the two rods are configured to split an electric field between them. The invention further related to a method of preparing an electrospun fiber by electrospinning comprising (i) extruding one or more solutions from electrified trips of two spinnerets, each of which comprises at least one tip electrified with an opposite charge to a tip of the other spinnerets, and (ii) collecting the extruded solution on a part of a collector comprising two rods and a platform connecting the two rods, wherein the two rods are grounded. In some embodiments, the method of preparing an electrospun fiber further comprises applying an accessory polymer to the solution (e.g. as a copolymer, blend, or melt). An "accessory polymer" refers to a polymer that may be added to the electrospun fibers and have any effect on their physical, chemical, and/or biological properties (e.g. tensile strength, hydrophillicity, biocompatibility). For example, the accessory polymer may be selected from the group consisting of polycaprolactone, poly(glycolic acid), poly (lactic acid), polydioxanone, poly (lactide-co-glycolide) copolymers, polyesters polysaccharides, polyhydroxyalkanoates, starch, polylactic acid, cellulose, proteins, agar, silks, alginate, collagen/gelatin, carrageenan, elastin, pectin, resilin, konjac, adhesives, gums, polyamino acids, polysaccharides, soy, zein, wheat gluten, casein, chitin/chitosan, serum albumin, hyaluronic acid, lipids/s urfactants, xanthan, acetoglycerides, waxes, surfactants, dextran, emulsan, gelian, polyphenols, levan, lignin, curd, ian, tannin, polygalactosamine, humic acid, shellac, pullulan, poly-gamma-glutamic acid, elsinan, natural rubber, yeast glucans, and synthetic polymers from natural fats and oils.

In one aspect, the method of preparing the electrospun fiber(s) according to some embodiments of the present invention may further comprise crosslinking the electrospun fiber(s). In some embodiments, the crosslinking may be performed by any conventional chemical crosslinking method (e.g. chemical reagent-promoted, chemically reactive linker-promoted and/or enzyme-promoted) and/or dehydrothermal crosslinking method (e.g. heat-promoted condensation), forming the covalently crosslinked electrospun fiber(s). In additional embodiments, the crosslinking comprises applying a cross-linking agent to the polymer or oligomer solutions to be electrospun. For example, the cross-linking agent may be selected from the group consisting of 1-Ethyl-3-(3-dimethylaminopropyl)carbodiimide (EDC), EDC/hyaluronic acid, genipin, and glutaraldehyde.

In some embodiments, a method of preparing an electrospun fiber further comprises adding a bioactive factor to the solution. A "bioactive factor" refers to protein, carbohydrate, or mineral that has any effect on a cellular activity. Examples of bioactive factors include, but are not limited to, an osteogenic growth factor, collagen, glycosaminoglycans, osteonectin, bone sialo protein, an osteoinductive factor, a chondrogenic factor, a cytokine, a mitogenic factor, a chemotactic factor, a transforming growth factor (TGF), a fibroblast growth factor (FGF), an angiogenic factor, an insulin-like growth factor (IGF), a platelet-derived growth factor (PDGF), an epidermal growth factor (EGF), a vascular endothelial growth factor (VEGF), a nerve growth factor (NGF), a neurotrophin, a bone morphogenetic protein (BMP), osteogenin, osteopontin, osteocalcin, cementum attachment protein, erythropoietin, thrombopoietin, tumor necrosis factor (TNF), an interferon, a colony stimulating factor (CSF), stem cell derived factor-1 (SDF-1), or an interleukin, among others. The bioactive factor may be a BMP, PDGF, FGF, VEGF, TGF, insulin, among others. Examples of BMPs include but are not limited to BMP-2, BMP-3, BMP-4, BMP-5, BMP-6, BMP-7, BMP-8, BMP-9, BMP-10, BMP-11, BMP-12, BMP-13, BMP-14, BMP-15, truncated BMPs described in PCT/US2012/053584, which is incorporated by reference in its entirety herein, and a mixture thereof.

The invention further relates to a scaffold comprising an aligned fiber. The invention further relates to a scaffold comprising one or more electrospun fibers. In some embodiments, a fast Fourier transform (FFT) analysis result of the fibers have adjacent major peaks with about 180° apart from each other. The "major peaks" herein refer to peaks higher than the average of the peaks in the result.

In one aspect, the scaffold may essentially consist of the aligned fiber and/or electrospun fiber. In another aspect, the scaffold may consist of the aligned fiber and/or electrospun fiber. The scaffold described herein may be biocompatible. A biocompatible matrix scaffold may be non-toxic, non-eliciting or stimulating severe inflammatory response or immunological rejections, and/or devoid of other undesired reactions at the implantation site.

Figure 8B:
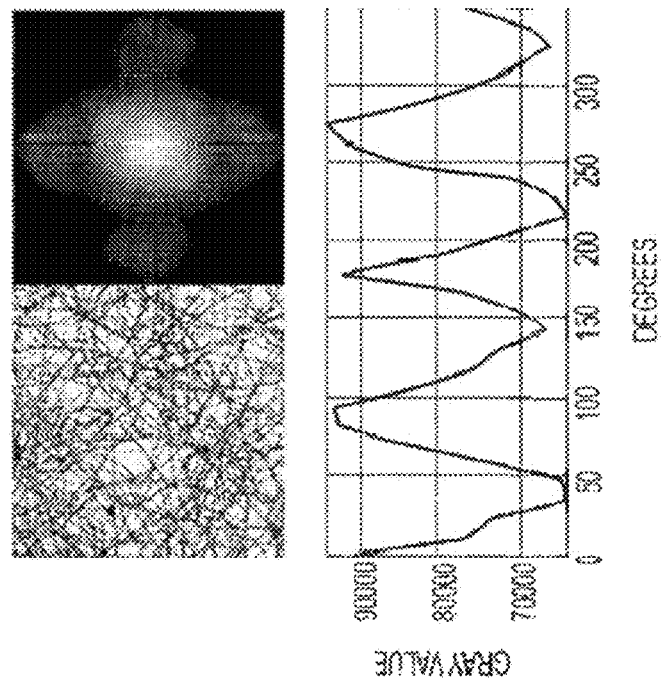
FIG. 8 depicts exemplary FFT analysis results (a) of the fibers described herein and (b) a control sample.
Figure 8A:
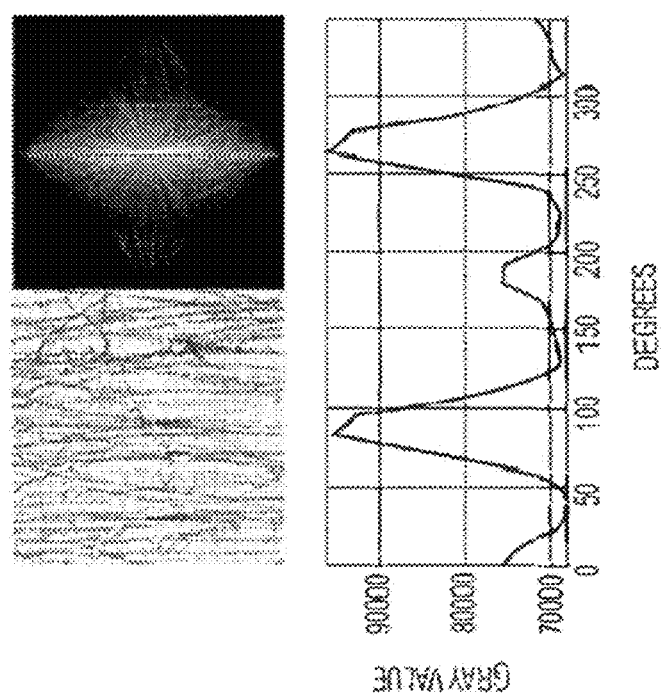

Alignment of the fibers in the scaffold may be measured by a fast Fourier transform (FFT) analysis. For example, the FFT analysis may be performed by the methods described in *Measuring fiber alignment in electrospun scaffolds: a user's guide to the 2D fast Fourier transform approach*, Ayres C E, Jha B S, Meredith H, Bowman J R, Bowlin G L, Henderson S C, Simpson D G. J Biomater Sci Polym Ed. 2008; 19(5):603-21, which is incorporated by reference in its entirety herein. In some embodiments, FFT result of the fibers described herein may have adjacent major peaks with about 180° apart from each other as shown in FIG. 8.

The aligned fiber, electrospun fiber, and/or scaffold of the present invention may comprise type I collagen. In some embodiments, total type I collagen may be present in the aligned fiber, electrospun fiber, and/or scaffold of the present invention in an amount from about 50% to about 95%, from about 60% to about 95%, from about 70% to about 95%, or from about 80% to about 95% by weight in it protein content. In additional embodiments, total type II collagen may be present in the aligned fiber, electrospun fiber, and/or scaffold of the present invention in an amount about 10% or less, about 5% or less, about 3% or less, or about 1% or less by weight in it protein content. In further embodiments, collagen type II may be absent from aligned fiber, electrospun fiber, and/or scaffold of the present invention. The types of collagen that are present or absent in the composition can be easily assessed using routine methods in the art. Methods of identifying and quantifying type of collagen are well known in the art, as disclosed, for example in Schnaper, H. W. and Kleinman, H. K., Pediatr. Neprol., 7:96-104 (1993), which is incorporated by reference.

In one aspect, the aligned fiber, electrospun fiber, and/or scaffold described herein may have less than about 8 wt %, 7 wt %, 6 wt %, 5 wt %, 4 wt %, 3 wt %, 2 wt %, or 1 wt % residual calcium. In another aspect, the average residual calcium amount in the aligned fiber, electrospun fiber, and/or scaffold described herein may be less than about 8 wt %, 7 wt %, 6 wt %, 5 wt %, 4 wt %, 3 wt %, 2 wt %, or 1 wt %.

In one aspect, the aligned fiber and/or electrospun fiber described herein may have a length from about 0.1 cm to about 10 cm, from about 1 cm to about 10 cm, from about 0.1 cm to about 20 cm, from about 1 cm to about 20 cm, from about 10 cm to about 20 cm, from about 0.1 cm to about 30 cm, from about 1 cm to about 30 cm, from about 10 cm to about 30 cm, from about 20 cm to about 30 cm, from about 0.1 cm to about 40 cm, from about 1 cm to about 40 cm, from about 10 cm to about 40 cm, from about 20 cm to about 40 cm, from about 30 cm to about 40 cm, from about 0.1 cm to about 50 cm, from about 1 cm to about 50 cm, from about 10 cm to about 50 cm, from about 20 cm to about 50 cm, from about 30 cm to about 50 cm, from about 40 cm to about 50 cm, 0.1 cm to about 60 cm, from about 1 cm to about 60 cm, from about 10 cm to about 60 cm, from about 20 cm to about 60 cm, from about 30 cm to about 60 cm, or from about 40 cm to about 60 cm. In another aspect, the total the aligned fiber and/or electrospun fiber in the scaffold described herein may have an average length from about 0.1 cm to about 10 cm, from about 1 cm to about 10 cm, from about 0.1 cm to about 20 cm, from about 1 cm to about 20 cm, from about 10 cm to about 20 cm, from about 0.1 cm to about 30 cm, from about 1 cm to about 30 cm, from about 10 cm to about 30 cm, from about 20 cm to about 30 cm, from about 0.1 cm to about 40 cm, from about 1 cm to about 40 cm, from about 10 cm to about 40 cm, from about 20 cm to about 40 cm, from about 30 cm to about 40 cm, from about 0.1 cm to about 50 cm, from about 1 cm to about 50 cm, from about 10 cm to about 50 cm, from about 20 cm to about 50 cm, from about 30 cm to about 50 cm, from about 40 cm to about 50 cm, 0.1 cm to about 60 cm, from about 1 cm to about 60 cm, from about 10 cm to about 60 cm, from about 20 cm to about 60 cm, from about 30 cm to about 60 cm, or from about 40 cm to about 60 cm.

In one aspect, the scaffold has an average porosity from about 60% to about 70%, from about 60% to about 80%, from about 60% to about 90%, from about 60% to about 95%, from about 70% to about 80%, from about 70% to about 90%, from about 70% to about 95%, from about 80% to about 90%, or from about 80% to about 95%.

In some embodiments, the aligned fiber, electrospun fiber, and/or scaffold comprises collagen type I, bone matrix, adipose extracellular matrix, heart basement membrane extract, heart basement membrane extracellular matrix, placenta basement membrane extract, placenta basement membrane extracellular matrix, brain-derived extracellular matrix, polycaprolactone, a biodegradable polymer, an accessory polymer described herein, or the mixture thereof.

In one aspect, the aligned fiber, electrospun fiber, and/or scaffold may comprise a bone matrix fiber comprising bone. In some embodiments, the bone matrix fiber may be prepared by the methods described in PCT/US2013/025226, which is incorporated herein in its entirety herein.

In another aspect, the aligned fiber, electrospun fiber, and/or scaffold may comprise heart basement membrane extract and/or heart basement membrane extracellular matrix. In some embodiments, the heart basement membrane extract and/or heart basement membrane extracellular matrix may be prepared by the methods described in PCT/US2011/49192, which is incorporated herein in its entirety herein. In an additional aspect, the placenta basement membrane extract and/or heart basement membrane extracellular matrix may be prepared by the same method to prepare the heart basement membrane extract and/or heart basement membrane extracellular matrix.

In another aspect, the aligned fiber, electrospun fiber, and/or scaffold may comprise a biodegradable polymer. The biodegradable, biocompatible polymers may include, but is not limited to, ethylene vinyl acetate, polyanhydricles, polyglycolic acid, collagen, polyorthoesters, and polylactic acid. The biodegradable, biocompatible polymers may further include a number of synthetic biodegradable polymers described herein.

In some embodiments, the aligned fiber and/or electrospun fiber in the scaffold is crosslinked. In additional embodiments, the aligned fiber, electrospun fiber, and/or scaffold comprises a bioactive factor described herein.

In additional embodiments, the aligned fiber, electrospun fiber, and/or scaffold may comprise an extracellular matrix component. For example, the extracellular matrix component may include, but is not limited to, collagen, glycosaminoglycans, osteocalcin, osteonectin, bone sialo protein, osteopontin, fibronectin, laminin, vitronectin, elastin or mixtures thereof.

In some embodiments, the scaffold of the present invention may further comprise a support. In additional embodiments, the fibers described herein may be attached to and/or cover the support.

In some embodiments, the scaffold of the present invention may be in a form of an elongated sheet or a composite of multiple layers of sheets similarly to the biocompatible matrix described herein. In additional embodiments, the scaffold may be prepared as shown in FIGS. 9A, 9B, and 9C. In one aspect, the materials for the elongated roll and the elongated sheet may be different. In another aspect, the materials for each elongated sheet in the multiple layers of sheets may be different from each other. In another aspect, the electrospun fibers in the scaffold are aligned in one direction. For example, the electrospun fibers in the scaffold are aligned in the direction parallel or perpendicular to the length of the elongated sheet or the multiple layers. In another aspect, the scaffold is prepared by folding or rolling the sheet or sheets, along with the direction of nano fiber alignment to form an elongated roll implant.

In some embodiments, the elongated roll implant may be prepared by combining a sheet or sheets to facilitate surgical implantation. The biomaterials to prepare the sheet and elongated roll may be the same, or different, as described previously.

In some embodiments, the elongated sheet scaffold described herein may have an average thickness of about 1000 µm or less, 900 µm or less, 800 µm or less, 700 µm or less, 600 µm or less, 500 µm or less, 400 µm or less, 300 µm or less, 200 µm or less, 100 µm or less, 50 µm or less, 20 µm or less, or 10 µm or less. In one aspect, the elongated sheet scaffold described herein may have an average thickness of about 1000 µm or more, 900 µm or more, 800 µm or more, 700 µm or more, 600 µm or more, 500 µm or more, 400 µm or more, 300 µm or more, 200 µm or more, 100 µm or more, 50 µm or more, 20 µm or more, 10 µm or more, or 1 µm or more.

In some embodiments, the length of the elongated sheet or roll implant scaffold is about 0.1 cm or more, about 0.3 cm or more, about 0.5 cm or more, about 0.7 cm or more, about 1 cm or more, about 2 cm or more, about 3 cm or more, about 5 cm or more, about 8 cm or more, about 10 cm or more, about 13 cm or more, about 15 cm or more, about 18 cm or more, about 20 cm or more, about 23 cm or more, about 25 cm or more, about 27 cm or more, or about 30 cm or more. In one aspect, the length of the elongated sheet or roll implant scaffold is about 1 cm or less, about 2 cm or less, about 3 cm or less, about 5 cm or less, about 8 cm or less, about 10 cm or less, about 13 cm or less, about 15 cm or less, about 18 cm or less, about 20 cm or less, about 23 cm or less, about 25 cm or less, about 27 cm or less, about 30 cm or less, about 40 cm or less, about 50 cm or less, or about 60 cm or less.

The scaffold according to some embodiments of the present invention may be used as an implant. An "implant" refers to any object that is designed to be placed partially or wholly within a patient's body for one or more therapeutic or prophylactic purposes such as for tissue augmentation, contouring, restoring physiological function, repairing or restoring tissues damaged by disease or trauma, and/or delivering therapeutic agents to normal, damaged or diseased organs and tissues. A "bone matrix implant" refers to a medical device or implant that includes a volume replacement material for augmentation or reconstruction to replace a whole or part of a bone structure. A predetermined shape of the implant may be varied to fit the implant site.

The invention further relates to methods culturing cells on the scaffold or aligned fiber described herein. In some embodiments, the cells are selected from the group consisting of stem cells, adipose derived stem cells, dental pulp stem cells, fibroblasts, and dorsal root ganglia.

For example, the invention provides for growing and/or culturing cells on a scaffold produced by the method described herein in vivo or in vitro. "Growing and/or culturing cells on a scaffold" includes traditional cell culture methods as well as placing on a surface in any setting, such as in natural or synthetic biocompatible matrices or tissues. In some embodiments, the cells that are cultured on the scaffold are stem cells. In further embodiments, the scaffold can be used in in vitro methods for supporting cell growth and proliferation as well as for increasing osteogenesis, chondrogenesis, or ligament/tendon genesis in the stem cells cultured on the scaffold.

Any cell described herewith may be cultured on a scaffold produced by the method described herein for between about 15 minutes and about 4 weeks, about 2 hours and about 2 weeks, about 2 hours and about 1 week, about 2 hours and about 72 hours, about 24 hours and about 72 hours, or about 24 hours and about 96 hours, at between about 20° C. and about 40° C. or about 30° C. and about 37° C., in an atmosphere containing between about 1% $CO_2$ and about 10% $CO_2$ or about 4% $CO_2$ and about 6% $CO_2$, in certain embodiments.

The invention also relates to methods of promoting nerve repair using the aligned fiber, electrospun fiber, and/or scaffold described herein. In some embodiments, the nerve repair includes, but is not limited to, central and peripheral nerve repair. The methods of promoting nerve repair may comprise implanting the aligned fiber, electrospun fiber, and/or scaffold into a nerve damaged site of a subject in need thereof. The method may further comprise culturing dorsal root ganglia and/or stem cells on the aligned fiber, electrospun fiber, and/or scaffold prior to the implanting. The stem cells, prior to culture on the scaffold of the present invention, may be undifferentiated or partially differentiated cells. The nerve regenerating activity of the aligned fiber, electrospun fiber, and/or scaffold may or may not be altered, including but not limited to, enhanced activity, relative to other scaffolds without the aligned and/or electrospun fiber described herein. The scaffolds for promoting nerve repair according to some embodiments of the present invention are in a form of an elongated sheet or a composite of multiple layers of sheets as discussed herein.

The invention also relates to methods of promoting osteoinductivity, with the methods comprising culturing cells on an aligned fiber, electrospun fiber, and/or scaffold produced by the method described herein. The cells, prior to culture on the aligned fiber, electrospun fiber, and/or scaffold of the present invention, may be undifferentiated or partially differentiated cells. The osteoinductive activity of the aligned fiber, electrospun fiber, and/or scaffold may or may not be altered, including but not limited to, enhanced activity, relative to other scaffolds without the aligned and/or electrospun fiber described herein.

The invention also relates to methods of promoting chondroinductivity, with the methods comprising culturing cells on a aligned fiber, electrospun fiber, and/or scaffold produced by the method described herein. The cells, prior to culture on aligned fiber, electrospun fiber, and/or scaffold of the present invention, may be undifferentiated or partially differentiated cells. The chondroinductive activity of the aligned fiber, electrospun fiber, and/or scaffold may or may not be altered, including but not limited to, enhanced activity, relative to other scaffolds without the aligned and/or electrospun fiber described herein.

The invention also relates to methods of promoting ligament/tendon differentiation, with the methods comprising culturing cells on an aligned fiber, electrospun fiber, and/or scaffold produced by the method described herein. The cells, prior to culture on the aligned fiber, electrospun fiber, and/or scaffold of the present invention, may be undifferentiated or partially differentiated cells. The ligament/tendon differentiation activity of the aligned fiber, electrospun fiber, and/or scaffold may or may not be altered, including but not limited to, enhanced activity, relative to other scaffolds without the aligned and/or electrospun fiber described herein.

In one aspect, in vitro alkaline phosphatase assays may be used to evaluate osteoinductivity in cells cultured on the scaffold prepared by the methods described herein. The ability of the aligned fiber, electrospun fiber, and/or scaffold prepared by the methods of the present invention to stimulate or induce the alkaline phosphatase expression in an otherwise non-bone forming cells, such as myoblast (C2C12 cells), would indicate that the aligned fiber, electrospun fiber, and/or scaffold of the present invention has osteoinductive activity. In these assays, cells cultured on other scaffolds without the aligned and/or electrospun fiber described herein are used as negative controls to show that the baseline alkaline phosphatase expression on non-bone forming cells. The baseline of the osteoblastic markers in the negative control need not be zero, meaning that the cells in the negative control group may have at least some level of phenotypic marker(s). Accordingly, an "osteoinductive" scaffold of the present invention would simply cause an increase in the osteoblastic markers in experimental cells over control grown on the other scaffolds without the aligned and/or electrospun fiber.

Moreover, osteoinductivity, chondroinductivity, and ligament/tendon differentiation may be determined in tissue culture by investigating the ability of the aligned fiber, electrospun fiber, and/or scaffold prepared by the methods of the present invention to differentiate or induce osteoblast phenotype, chondrocyte phenotype, ligament/tendon cell phenotype in cultured cells, such as primary cells, cell lines, or explants. For example, the cells may display increased production of a marker characteristic of osteoblasts and/or chondrocytes, such as alkaline phosphatase, etc. For example, the osteoinductive, chondroinductive, ligament/tendon differentiation potentials of the aligned fiber, electrospun fiber, and/or scaffold described herein may be more than 0.2, 0.4, 0.6, 0.8, 1, 2, 3, 4, 5, 6, 7, 8, 9 or 10 times greater than the fiber and/or scaffolds without the aligned and/or electrospun fiber. In another example, the osteoinductive, chondroinductive, ligament/tendon differentiation potentials of the culture on the scaffold and/or implant described herein may be more than 10, 20, 30, 40, 50, 60, 70, 80, 90, 100, 500 or even 1000 times greater than those of the aligned fiber, electrospun fiber, scaffold and/or implant without any aligned and/or electrospun fiber. Of course, this indicates that lower concentrations of modified growth factor, compared to unmodified growth factor are required to achieve the same effects.

Osteoinductivity, chondroinductivity, ligament/tendon differentiation, for assessing the bone, cartilage, ligament or tendon forming potential induced by the scaffold of the present invention in a location such as muscle, may also be evaluated using a suitable animal model.

The invention also relates to methods of promoting cell attachment, proliferation or maintaining the differentiated state or preventing de-differentiation of osteoblasts, chondrocytes, ligament cells, tendon cells and/or any cell type disclosed herein with the methods comprising culturing the cells on a scaffold produced by the method described herein. The proliferative activity of the aligned fiber, electrospun fiber, and/or scaffold may or may not be altered, including but not limited to, enhanced activity, relative to a fiber and/or scaffold without any aligned and/or electrospun fiber.

Mitogenicity may be assessed by investigating cell proliferation induced by the aligned fiber, electrospun fiber, and/or scaffold prepared by the methods of the present invention using various in vitro assays that measure metabolic activity, such as MTT [3-(4,5-dimethylthiazol-2-yl)-2,5-diphenyltetrazolium bromide] assay, alamarBlue® assay, and others. The alamarBlue® assay uses a non-cytotoxic reduction-oxidation indicator to measure cell metabolic activity, making it a nondestructive assay for assessing the mitogenic activity of the aligned fiber, electrospun fiber, and/or scaffold described herein.

The invention also relates to methods of increasing or promoting osteogenesis, chondrogenesis, or ligament/tendon genesis in cells. The methods may comprise culturing the cells on an aligned fiber, electrospun fiber, and/or scaffold produced by the method described herein. The osteogenic, chondrogenic, ligament, or tendon inducing activity of the aligned fiber, electrospun fiber, and/or scaffold may or may not be altered, including but not limited to, enhanced activity, relative to a fiber and/or scaffold without aligned and/or electrospun fiber described herein.

The invention also relates to methods of treating a tissue or organ defect or injury, for example, a musculoskeletal, dental or soft-tissue defect or injury, in an animal comprising administering (1) cells cultured on the scaffold produced by the methods described herein and/or (2) the aligned fiber, electrospun fiber, scaffold and/or implant described herein to the tissue or organ defect (e.g. osseous defects, defects in cartilage, ligament, tendon, spinal disk, and tendon insertion site to bone).

The invention further relates to methods of treating a tissue or an organ defect or injury, for example, including, but not limited to a musculoskeletal, dental or soft-tissue defect, or a nerve defect in an animal by applying a aligned fiber, electrospun fiber, and/or scaffold prepared by the methods described herein to the defect, and application to the defect may be accomplished by injecting the scaffold into the defect, inserting the aligned fiber, electrospun fiber, and/or scaffold between tissue or organ, or placing the aligned fiber, electrospun fiber, and/or scaffold on top of the defect. The present invention is also directed to treating a defect or injury in an organ by applying an aligned fiber, electrospun fiber, and/or scaffold to the defect. In one embodiment, the tissue defect may be treated by applying an elongated sheet described herein to surround the defect, or by applying an elongated roll implant described herein between the tissue defect or gap. The tissue defect or gap may be from the tissues including, but not limited to, bone, tendon, ligament, blood vessel, skin, intestine, nerve, and cartilage. Optionally, the elongated sheet may be applied around the tissue defect, and/or the elongated roll implant may be applied to facilitate surgery and healing. For example, the elongated implant roll may be applied between the tissue defect or gap, then the ends of the elongated implant roll may be sutured to the tissue. In some embodiments, the elongated sheet may be applied or sutured around the tissue defect or gap, covering the elongate implant roll and/or the suture sites of the elongated implant roll with tissues. In additional embodiments, the elongated roll may facilitate the tissue growth through the defect gap. The elongated sheet can prevent adhesion of the elongated implant roll with surrounding tissue or prevent undesirable tissue ingrowth, for example, scar formation, to interfere the tissue regeneration or remodeling. The biomaterials used for preparing the enlongated sheet and the enlongated implant roll may be same or different, depending on the specific surgery and tissue regeneration needs. The tissue defect may occur in tendon, ligament, nerve and other tissue types enlisted previously.

In yet another embodiment, cells may be seeded onto an aligned fiber, electrospun fiber, and/or scaffold prepared by the methods provided herein. The cells seeded on the scaffold can be any cell, such as but not limited to, dorsal root ganglia, osteoblasts, chondrocytes, ligament cells, tendon cells, progenitor cells, and stem cells disclosed herein or otherwise known in the art. The seeded cells may be allowed to proliferate and possibly attach to the matrix. Methods of seeding cells onto matrices, such as collagen matrix coated with the aligned fiber, electrospun fiber, and/or scaffold prepared by the methods provided herein, are well known in the art.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents and patent applications referred to in this application are herein incorporated by reference in their entirety herein.

The following examples are illustrative and are not intended to limit the scope of the invention described herein.

Example 1

1,1,1,3,3,3-hexafluoro-2-propanol (HFP) (CAS#920-66-1) was from Acros Organics (Geel, Belgium, acros.com). Polycaprolactone (PCL) (B6003-1, B6003-2) was from Durect Lactone (Pelham, Ala., absorbables.com). The electrospinning apparatus was designed using an Aladdin Programmable Syringe Pump from World Precision Instruments, Inc. (Sarasota, Fla., wpiinc.com) and two adjustable high voltage power supplies from Gamma High Voltage Research (Ormond Beach, Fla.). The aligned metal rods used in the rotating motor, or statically, may be of steel, stainless steel, copper, or other heavy metal. A Mercotac® connector (#110T and 110TS) was used as an electrically conductive bearing. The following items were purchased from McMaster-Carr:

8965K42 Ultra Conductive Copper (Alloy 101) Rod, ¼" Diameter
1256T14 Multipurpose Stainless Steel (Type 304) Mirror Finish #8, ¼" Diameter
88855K51 High-Strength Stainless Steel (Type 17-4 Ph) ¼" Diameter
86985K31 High-Strength Aluminum (Alloy 2024) ¼" Diameter
8965K86 Ultra Conductive Copper (Alloy 101) Tube, ¼" OD, 0.186" ID, 0.032" Wall Thk
8457K536 Stainless Steel Shape Type 304/304L, Round Tube, ¼" OD
1968T11 High-Strength Aluminum Tube (Alloy 2024) ¼" OD, 0.180" ID, 0.035" Wall Thickness
2706A4 Tube Cutter ¼" to 1⅝" Tube OD, 6" Open/Closed Length
4575N3 Miniature Flange-Mounted SS Ball Bearing Shielded, for ¼" Shaft Diameter
6384K352 Steel Ball Bearing Flanged Double Sealed for ¼" Shaft Dia, ¹¹⁄₁₆" OD
8600N3 Miniature Alum Base-Mnt SS Ball Brng—ABEC-3 for ¼" Shaft Diameter
7200K3 NEMA 34 Face-Mount Brushless DC Motor ⅓ hp, 3450 rpm, Integrated Speed Control
6099K41 Stainless Steel One-Piece Set-Screw Coupling ½" Bore, 1½" Length, 1" OD, with Keyway
8774K33 Static-Dissipative Clear Cast Acrylic Sheet ¼" Thick, 12"×24" 97042A516 18-8 Stainless Steel One-End Threaded Stud ½"-13×⅝"×1½"
99223A067 Acetal Hex Nut ½"-13 Thread
94564A023 Nylon Flat Point Socket Set Screw 6-32×¼"
99861K21 Black Delrin Rod 4" Diameter, ½" Length
8576K15 Black Delrin Rod ½" Diameter, 5' Length
94922A050 Nylon 6/6 Acorn Nut Off-White, ½"-13 Thread Size, ¾" W, ¹³⁄₁₆" H
8572K61 White Delrin Rod 1" Diameter, 1' length
85821K21 White Delrin Rod 4" Diameter, ½" Length
8572K55 White Delrin Rod ½" Diameter
93140A839 Polycarbonate Machine Screw Flat Head Slotted, ¼"-20×¾"
95868A148 Nylon 6/6 SHCS 6-32 Thread, ½" Length, Off-White
7643A421 1"×30', Gray, 0.012" Thk, High-Temp Self-Fusing Silicone Rubber Tape
7586K12 Adhesive-Backed Cable Holder Press in, ¼" Maximum Bundle
60015K42 Tear-Resistant Rubber Vibration Damping Pad 6"×6"×⅜" Thick, 45 PSI Max Load
4056K42 Oil-Resistant Nitrile Vibration Damping Pad 6"×6"×⁵⁄₁₆" Thick, 100 PSI Max Load
94605A541 Nylon 82 Deg Flat Head Slotted Machine Screw ¼"-20×¾"
94564A080 Nylon Flat Point Socket Set Screw ¼"-20×½"
5537K26 Tinned Copper Expandable Mesh Sleeving ¼" ID, ³⁄₁₆" to ⁵⁄₁₆" Bundle Dia
8491A614 Steel Press-Fit Drill Bushing/Liner 0.257" (F) ID, ¹³⁄₃₂" OD, ½" Length
3504T21 Push-on Round FDA Cap Fits ⅜" OD, ½" Inside Height
92805K22 Push-on High-Temperature Silicone Rubber Cap Fits 0.6" Outside Diameter, 1½" Inside Height A high voltage power supply source was used to apply a +10-40 kV DC voltage to parallel metal rods, with a −5-40 kV DC field applied to the syringe/needle containing a polymer solution, with syringe placed in a syringe pump. The metal posts can be hollow or solid, and have been tested as rods of stainless steel, steel, copper, and aluminum, both solid and hollow using thin-walled tubing. The absolute DC field strength ranged from 15 kV to 60 kV. A programmable syringe pump was set to dispense the solution at 0.50-9.50 mL/hr, ideally at 6.5 ml/hr for pure PCL, and 3 ml/hr for heart basement membrane (HBM) and HBM/PCL mixtures. After approximately 5 minutes to 1 hour of electrospinning, the aligned fibers are collected for imaging (SEM and DIC).

Metal rods were used to align electrospun PCL. PCL dissolved in HFP (100 mg/ml) at a +15 kV reference, set 15 cm apart, was electrospun between the rods, with PCL pumped at 5 ml/hr over 5 minutes to the form the aligned nanofibers seen collecting between the rods. FIG. 1 (a, d)

shows the representative electric field lines and the know bending of these lines in a field with a split point charge (as simplified plane of point charges represented). This splitting of the electric charge field is believed to act on imparting alignment as they travel on the looping fibers in this warped electrostatic field. We have successfully aligned fibers with hollow and solid metal rods, and the modulation of the electric field lines by solid vs. hollow rods is also shown (FIGS. 1b and 1c) (electric field diagrams created using the applet from cco.caltech.edu/~phys1/java/phys1/EField/EField.html).

Figure 2:
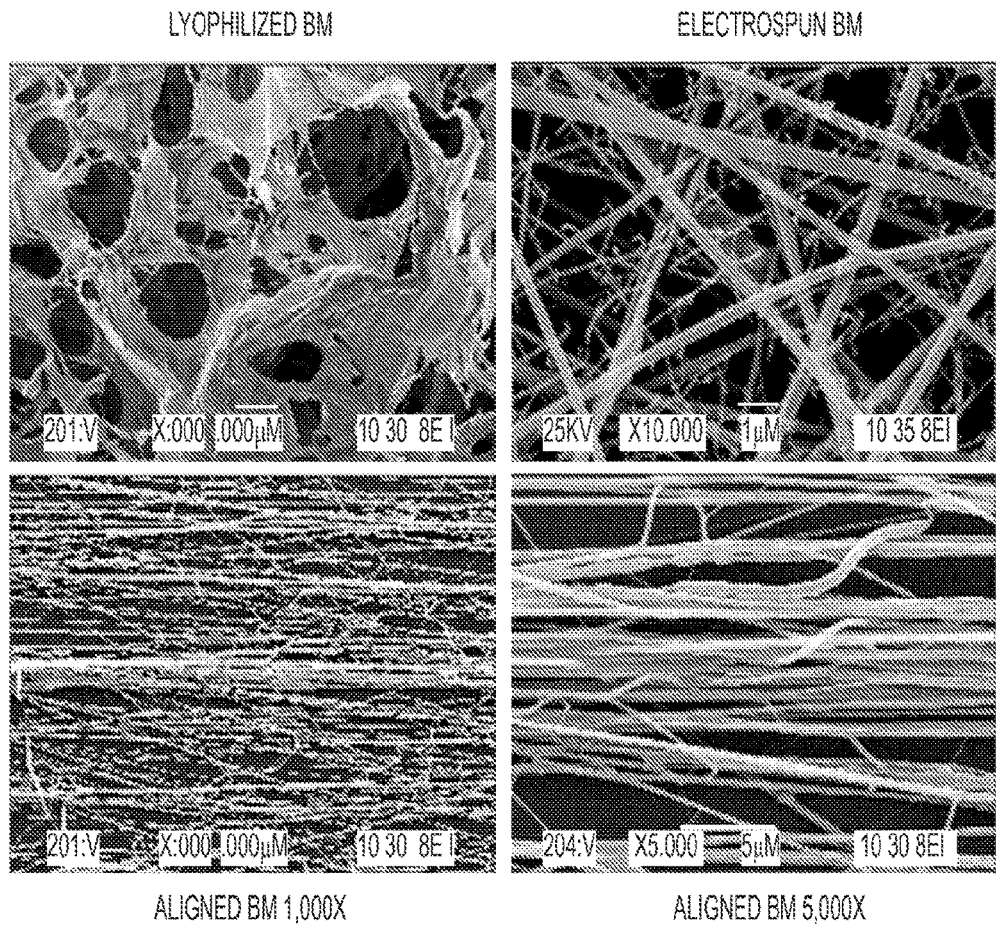
FIG. 2 depicts raw basement membrane (top left) next to it randomly electrospun architecture (to right), as compared to aligned basement membrane generated by parallel charged rod aligned electrospinning (bottom left and right).
Figure 3:
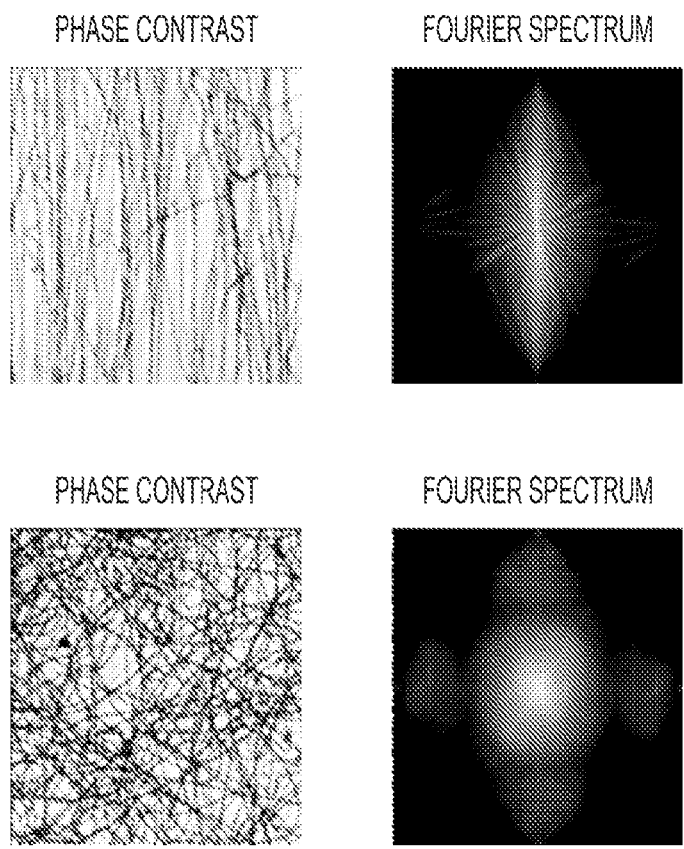
FIG. 3 depicts a Fourier spectrum from charged rod aligned and randomly electrospun fibers. The aligned pattern/texture recognition is typical to that of a regular, repeating line pattern, with the random fibers consistent with random noise generation spectra, as commonly seen in pattern recognition from FFT analysis.

For SEM images, aligned electrospun PCL and HBM/PCL blended samples were taken from the aligned rods and mounted on aluminum stubs using carbon stickers. The samples were then coated with gold at about 50 nm thickness using a plasma-based sputter coater. Coated samples were imaged using a JOEL 6400 scanning electron microscope (SEM) with Orion image processing. Representative images of charged parallel rod aligned fibers, as compared to fibers generated in the traditional, randomly aligned fashion by collection onto a static piece of grounded foil, can be seen in FIG. 2. The average cross-sectional fiber diameter of the electrospun fibers generated from random and charged rod aligned basement membrane matrix was calculated by measuring 35 unique points in ImageJ64 (NIH shareware), with results shown in FIG. 2, along with the average angle of the fibers. A fast Fourier transform (FFT) was performed to indicate the degree of alignment as seen in FIG. 3 using the ImageJ64 FFT tool, with patterns of aligned fibers shown to match with those of know aligned Fourier spectra, as commonly used for pattern recognition.

Figure 4:
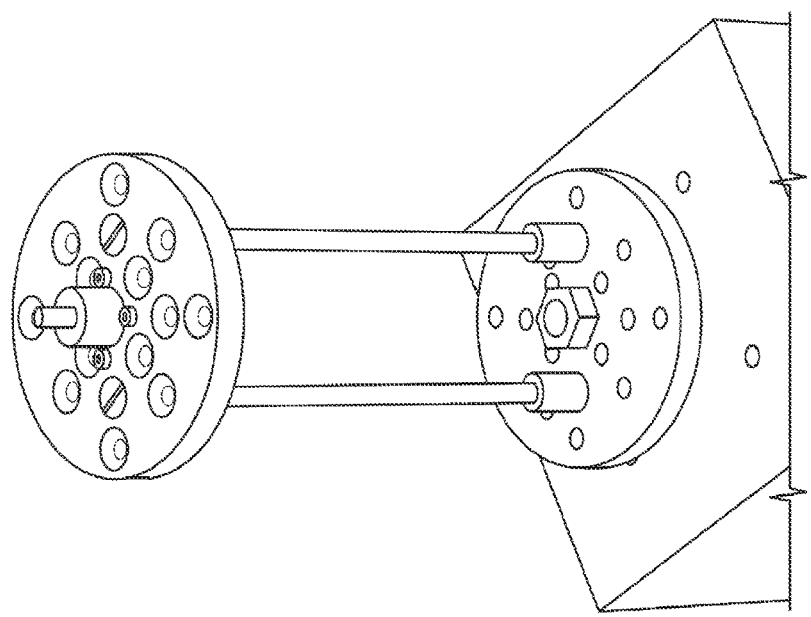
FIG. 4 depicts a modeling of a rotating parallel rod mandrel having a mercury coupled bearing inserted into the top of the device to split the electrical charge between the rods.
Figure 4:
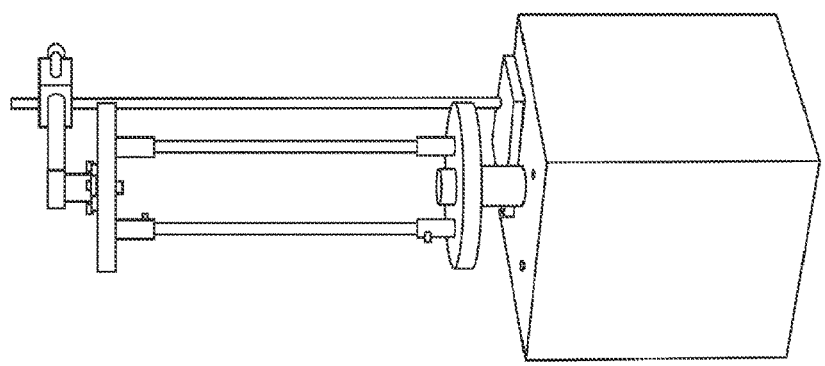
Figure 4:
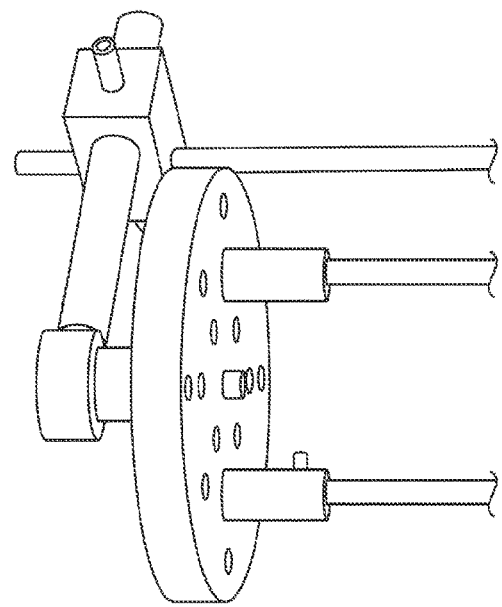
Figure 5:
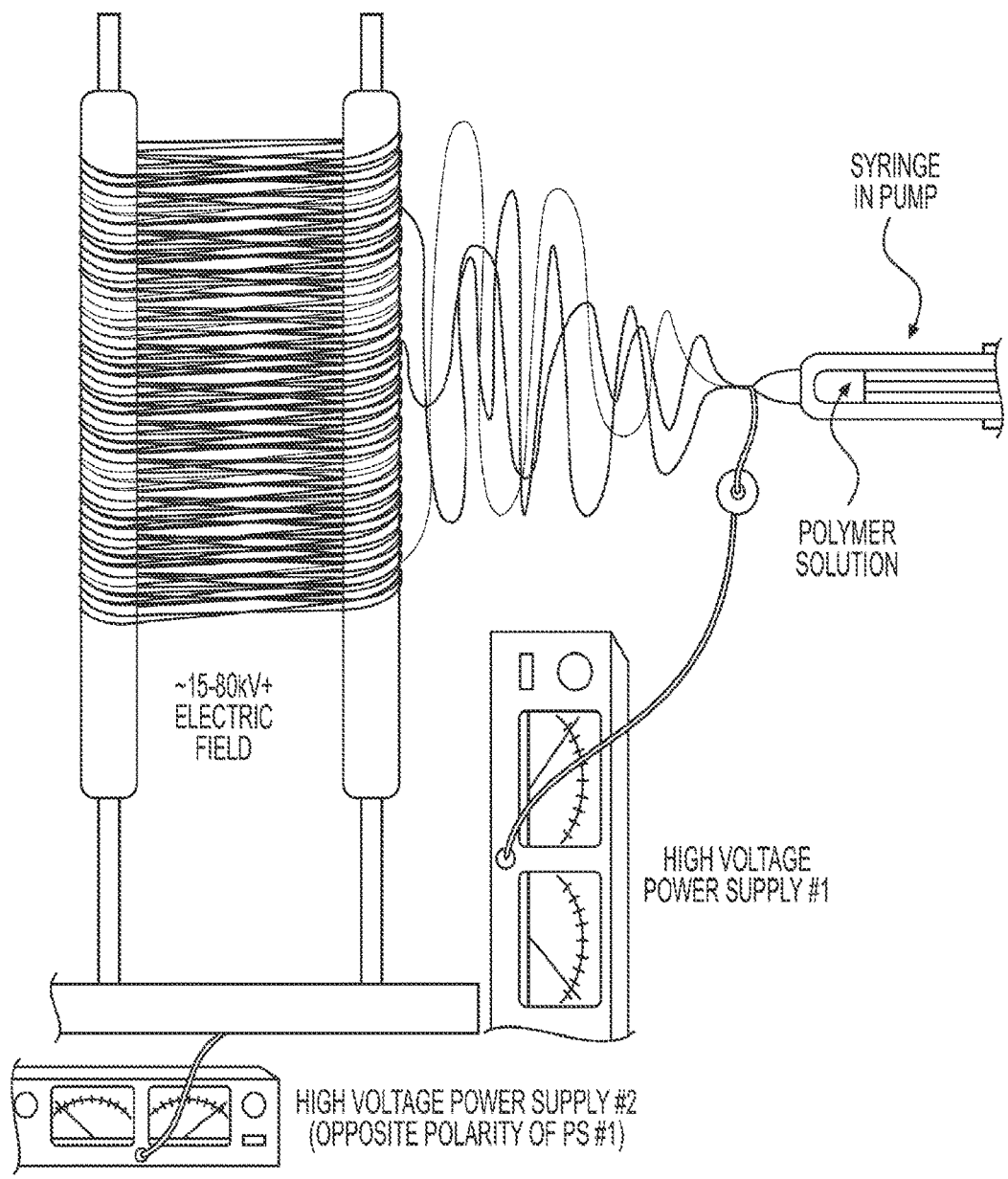
FIG. 5 depicts the exemplary elements of the parallel electric charged rod electrospinning setup. Using two charged rods imparts alignment to the traveling fibers, optionally through the point charge splitting of the electric field.

FIG. 4 illustrates a design for rotating the charged parallel rods using a mercury coupled bearing to allow electrical conductance with the rotating charged rods mounted in plastic platforms attaching to a high speed motor (0-4000 RPMs). The actual implementation of this rotating rod design is shown in FIG. 5. In another aspect, this rotating charged parallel point charged rod fiber alignment process may be modified so that electrospun fibers of opposite charge are propelled towards each other in the static field, whereby the fibers combine in a "whirlpool" fashion roughly equidistant apart in space. In this arrangement, the fiber charges are effectively neutralized and the fibers are then collected on the grounded rotating rods of the mandrel, which allows a thicker layer of fibers to be collected due to less fiber-to-fiber charge repulsion. Equally charged fibers are believed to have a repulsive effect on each other in the collected fibers. Charge neutralization of the fibers in this fashion theoretically negates this phenomenon to electrospin sheets that are up to about 1.5 times, 2.0 times, 3.0 times, or 3.4 times the thickness of conventionally electrospun fiber sheets. For example, two syringe pumps with basement membrane, each attached to a high voltage power supply may have one supply set to positive (+) voltage, and the other set to negative (−) voltage to generate the static electric field for electrospinning, with fibers collected on the rotating or static charged rods. The charges of equal voltage and opposite charge combine in space above the dual charged rod mandrel in a the vortex of the electric field, depositing as charge neutralized fibers on the rods, which allows for enhanced thickness of the collected aligned fibers over conventional methods.

By implementing a pneumatic motor in the conformations for electrospinning aligned (and random) nanofibers onto a mandrel as described above, on average 9.24% more material is collected on the mandrel(s) compared to using an electrical motor.

Example 2: Heart Base Membrane Fiber Scaffold

Figure 6:
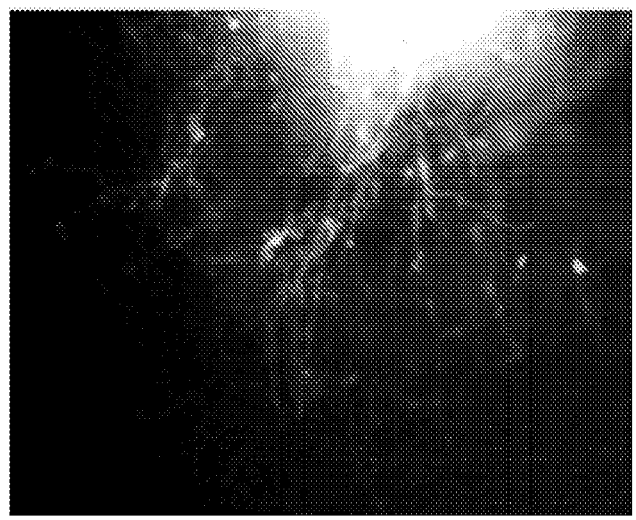
FIG. 6 depicts aligned heart base membrane fiber scaffold that allow dorsal root ganglia attachment and outgrowth.
Figure 6:
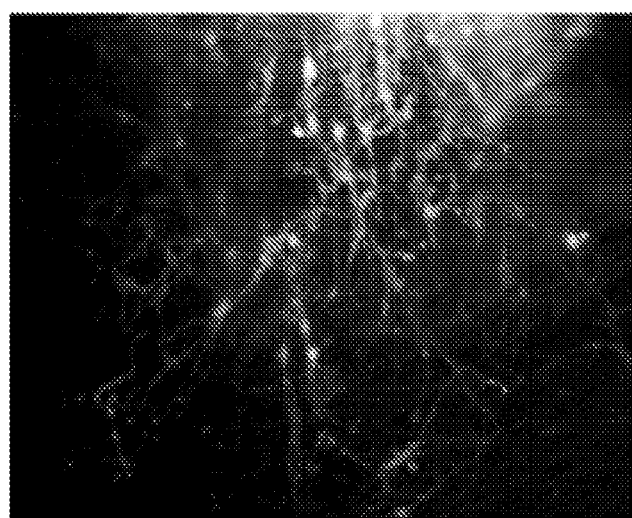
Figure 7:
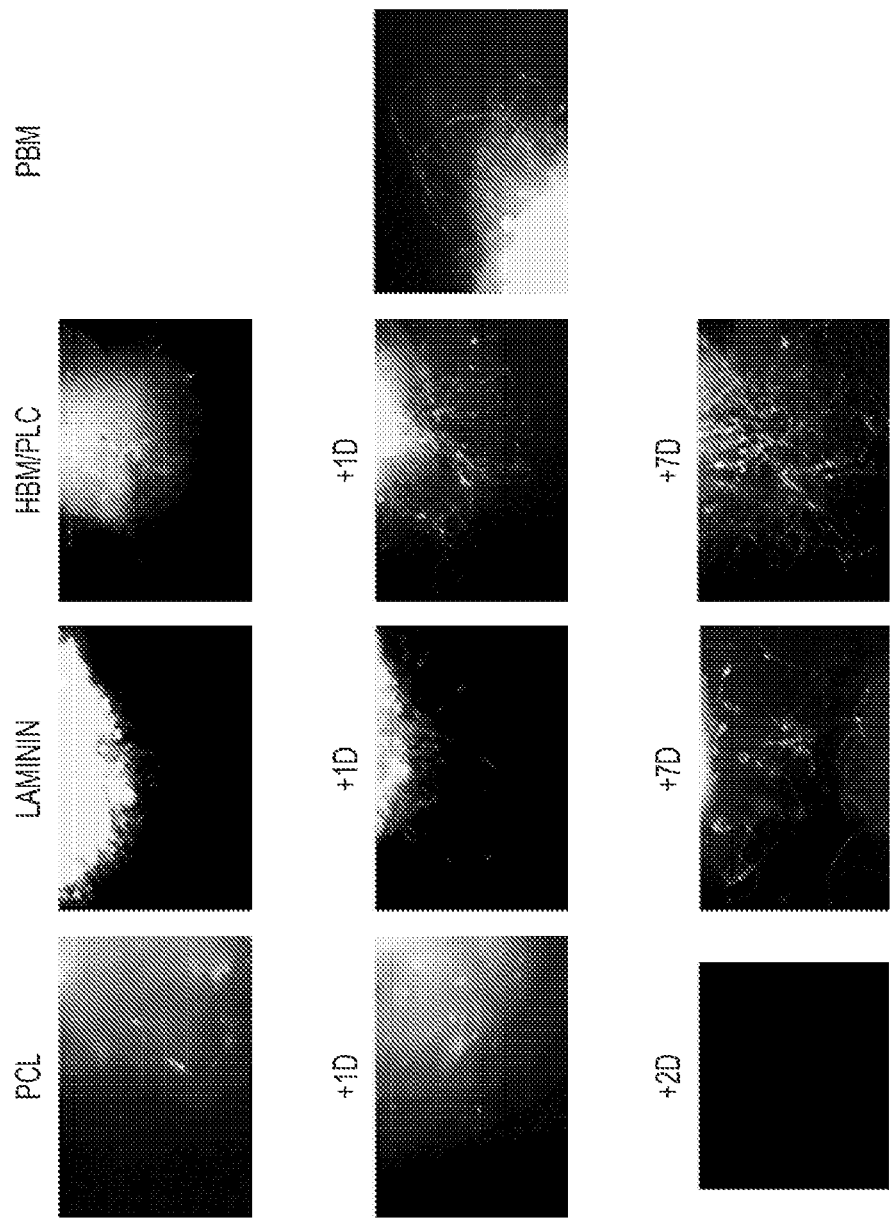
FIG. 7 depicts aligned placenta and heart base membrane fiber scaffolds that allow dorsal root ganglia attachment and outgrowth.

Heart basement membrane (HBM) and polycaprolactone (PCL) were dissolved separately in HFP at 100 mg/ml, and mixed in a 10% ratio of HBM:PCL (0.100 g HBM to 0.900 g PCL), mixed at 4 deg a total of 2 hrs until fully into solution. The HBM:PCL was loaded into a glass 5 ml syringe, loaded into a syringe pump set to expel at 1.5 ml/ml, in a static+20 kV electric field at the needle and −10 kV to each of the parallel aligned collecting rods, then electrospun between the poles in a highly aligned fashion. The aligned fibers of HBM/PCL were collected and stored in a dessicator prior to use. To obtain dorsal root ganglion (DRGs), an 11 day old YFP-βIII Tubulin expressing transgenic mouse was sacrificed for collection of the spinal cord and removal of the DRGs, which were liberated from their capsule and briefly digested in trypsin, then placed upon the aligned HBM:PCL scaffold and cultured in basic neuron media containing B27 supplement. As shown in FIG. 6, outgrowths from the DRGs were visualized under light and fluorescent microscopy at 1 and 2 days post explantation, with aligned neurons seen erupting from the bundle, with the neurite outgrowths seen tracing the aligned fibers.

Example 3: Dorsal Root Ganglia Attachment and Outgrowth on Placenta and Heart Basement Membrane Nanofibers Heart basement membrane HBM an—d polycaprolactone (PCL) were dissolved separately in HFP at 100 mg/ml, and mixed in a 10% ratio of HBM:PCL (0.100 g HBM to 0.900 g PCL), mixed at 4 deg a total of 2 hrs until fully into solution. Each biopolymer was individually loaded into a glass 5 ml syringe, loaded into a syringe pump set to expel at 2.5 ml/hr, in a static+20 kV electric field at the needle, then electrospun onto 10 mm glass coverslips backed by a grounded piece of foil. The randomly aligned fibers were collected and stored in a dessicator prior to use. To obtain dorsal root ganglion (DRGs), a 10 day old YFP-βIII Tubulin expressing transgenic mouse was sacrificed for collection of the spinal cord and removal of the DRGs, which were liberated from their capsule and briefly digested in trypsin, then placed upon the scaffolds and cultured in basic neuron media containing B27 supplement for 7 days. As shown in FIG. 6, Outgrowths from the DRGs were again visualized under light and fluorescent microscopy at 1-7 days post explanation. Neurite outgrowth was seen tracing the electrospun fibers on HBM/PCL coated coverslips.

Example 4: Dorsal Root Ganglia Attachment and Outgrowth on Polycaprolactone Nanofibers (Comparative Example)

Polycaprolactone (PCL) was dissolved in HFP at 100 mg/ml and mixed by vortexing at room temperature for 2 hrs until fully into solution. The PCL biopolymer was loaded into a glass 5 ml syringe, loaded into a syringe pump set to expel at 5 ml/h, in a static+20 kV electric field at the needle, then electrospun onto 10 mm glass coverslips backed by a grounded piece of foil. The randomly aligned fibers of each group were collected and stored in a dessicator prior to use. To obtain dorsal root ganglion (DRGs), an 10 day old YFP-βIII Tubulin expressing transgenic mouse was sacrificed for collection of the spinal cord and removal of the DRGs, which were liberated from their capsule and briefly digested in trypsin, then placed upon the scaffolds and cultured in basic neuron media containing B27 supplement for 7 days (n=3). Outgrowths from the DRGs were visualized under light and fluorescent microscopy at 1-7 days post explantation. DRGs did not grow out on PCL and were found to be non-viable after 2-3 days in repeat trials (n=6).

The invention claimed is:

1. A scaffold comprising one or more electrospun fibers comprising collagen, wherein a fast Fourier transform (FFT) analysis result of the fibers have adjacent major peaks with about 180° apart from each other.

2. The scaffold according to claim 1, wherein the fibers comprise type I collagen in its native triple helical structure.

3. The scaffold according to claim 1, wherein the fiber has less than about 8 wt % residual calcium.

4. The scaffold according to claim 1, wherein the scaffold has an average porosity from about 60% to about 90%.

5. The scaffold according to claim 1, wherein the scaffold comprises collagen type I, bone matrix, adipose extracellular matrix, heart basement membrane extract, heart basement membrane extracellular matrix, placenta basement membrane extract, placenta basement membrane extracellular matrix, brain-derived extracellular matrix, polycaprolactone, an accessory polymer, or the mixture thereof.

6. The scaffold according to claim 5, wherein the accessory polymer is selected from the group consisting of polycaprolactone, poly(glycolic acid), poly(lactic acid), polydioxanone, poly(lactide-co-glycolide) copolymers, polyesters polysaccharides, polyhydroxyalka noates, starch, polylactic acid, cellulose, proteins, agar, silks, alginate, collagen/gelatin, carrageenan, elastin, pectin, resilin, konjac, adhesives, gums, polyamino acids, polysaccharides, soy, zein, wheat gluten, casein, chitin/chitosan, serum albumin, hyaluronic acid, lipids/surfactants, xanthan, acetoglycerides, waxes, surfactants, dextran, emulsan, gelian, polyphenols, levan, lignin, curd, ian, tannin, polygalactosamine, humic acid, shellac, pullulan, poly-gamma-glutamic acid, elsinan, natural rubber, yeast glucans, synthetic polymers from natural fats and oils.

7. The scaffold according to claim 1, wherein the scaffold comprises a bioactive factor.

8. The scaffold according to claim 7, wherein the bioactive factor is selected from the group consisting of an osteogenic growth factor, collagen, glycosaminoglycans, osteonectin, bone sialo protein, an osteoinductive factor, a chondrogenic factor, a cytokine, a mitogenic factor, a chemotactic factor, a transforming growth factor (TGF), a fibroblast growth factor (FGF), an angiogenic factor, an insulin-like growth factor (IGF), a platelet-derived growth factor (PDGF), an epidermal growth factor (EGF), a vascular endothelial growth factor (VEGF), a nerve growth factor (NGF), a neurotrophin, a bone morphogenetic protein (BMP), osteogenin, osteopontin, osteocalcin, cementum attachment protein, erythropoietin, thrombopoietin, tumor necrosis factor (TNF), an interferon, a colony stimulating factor (CSF), stem cell derived factor-1 (SDF-1), and an interleukin.

9. The scaffold according to claim 1, wherein the scaffold comprises an extracellular matrix component.

10. The scaffold according to claim 9, wherein the extracellular matrix component is selected from the group consisting of collagen, glycosaminoglycans, osteocalcin, osteonectin, bone sialo protein, osteopontin, fibronectin, laminin, and mixtures thereof.

11. A method of cell culture comprising culturing cells on the scaffold according to claim 1 under conditions suitable for the cell culture.

12. The method of claim 11, wherein the cells are selected from the group consisting of stem cells, adipose derived stem cells, dental pulp stem cells, fibroblasts, and dorsal root ganglia.

13. A method of promoting differentiation of stem cells into osteoblasts, chondrocytes, ligament or tendon, the method comprising culturing the cells on the scaffold according to claim 1 under conditions suitable for the cell differentiation.

14. The method of claim 13, wherein the stem cells are progenitor cells or adult stem cells.

15. The method of claim 14, wherein the progenitor cells or the adult stem cells are derived or isolated from placenta, bone marrow, adipose tissue, blood vessel, amniotic fluid, synovial fluid, synovial membrane, pericardium, periosteum, dura, peripheral blood, umbilical blood, menstrual blood, baby teeth, nucleus pulposus, brain, skin, hair follicle, intestinal crypt, neural tissue, or muscle.

* * * * *